(12) United States Patent
Ding et al.

(10) Patent No.: US 8,540,845 B2
(45) Date of Patent: Sep. 24, 2013

(54) METHOD AND SYSTEM FOR STABILIZING DRY-BASED DENSITY OF WOOD CHIPS TO BE FED TO A CHIP REFINING PROCESS

(75) Inventors: Feng Ding, Québec (CA); Claude Lejeune, Québec (CA)

(73) Assignee: Centre de Recherche Industrielle du Quebec

( * ) Notice: Subject to any disclaimer, the term of this patent is extended or adjusted under 35 U.S.C. 154(b) by 163 days.

(21) Appl. No.: 13/095,224

(22) Filed: Apr. 27, 2011

(65) Prior Publication Data

US 2011/0264258 A1 Oct. 27, 2011

Related U.S. Application Data

(60) Provisional application No. 61/328,467, filed on Apr. 27, 2010.

(51) Int. Cl.
*D21C 7/14* (2006.01)

(52) U.S. Cl.
USPC .............. 162/49; 162/262; 162/48; 700/100; 700/127

(58) Field of Classification Search
USPC ............. 162/49, 48, 262; 700/104, 127–129, 700/214; 702/81
See application file for complete search history.

(56) References Cited

U.S. PATENT DOCUMENTS

| | | | |
|---|---|---|---|
| 3,947,668 A | 3/1976 | Al-Shaikh et al. | |
| 3,983,403 A | 9/1976 | Dahlström et al. | |
| 4,148,439 A | 4/1979 | Flodén | |
| 4,184,204 A | 1/1980 | Flohr | |
| 4,301,373 A | 11/1981 | Sjödin | |
| 4,392,204 A | 7/1983 | Prim et al. | |
| 4,498,137 A | 2/1985 | Flohr | |
| 4,500,203 A | 2/1985 | Bieringer | |
| 4,661,911 A | 4/1987 | Ellery, Sr. | |
| 4,691,365 A | 9/1987 | Nagashima | |
| 4,692,210 A | 9/1987 | Forrester | |

(Continued)

FOREIGN PATENT DOCUMENTS

| | | |
|---|---|---|
| EP | 445321 B1 | 6/1994 |
| WO | 9420671 A1 | 9/1994 |

OTHER PUBLICATIONS

Du Huaijing, Multivariable Predictive Control of a TMP Plant, A Thesis submitted in partial fulfillment of the requirements for the degree of Doctor of Philosophy, The University of British Columbia, Oct. 1998.*

(Continued)

*Primary Examiner* — Mark Halpern
(74) *Attorney, Agent, or Firm* — Jean-Claude Boudreau

(57) ABSTRACT

A method and system for stabilizing dry-based density of wood chips from several sources feeding a chip processing stage upstream of a chip refining process, perform on-line estimation of a set of wood chip properties characterizing the wood chips, including light reflection-related property, moisture content and dry-based density, which are used by a reference model capable of comparing the estimated dry-based density with a predetermined target to produce error data, and selectively modifying discharge rate set points of one or more of the wood chip sources to minimize the error data within fluctuation limits around the target. The discharge rate of the wood chip sources is controlled in accordance with the set points to substantially stabilize the dry-based density of the wood chips.

14 Claims, 17 Drawing Sheets

(56) References Cited

U.S. PATENT DOCUMENTS

| | | | |
|---|---|---|---|
| 4,803,371 A | 2/1989 | Durland | |
| 4,806,014 A | 2/1989 | Einarson et al. | |
| 4,886,576 A | 12/1989 | Sloan | |
| 4,943,347 A | 7/1990 | Floden | |
| 5,011,088 A | 4/1991 | Savonjousi | |
| 5,011,090 A | 4/1991 | Savonjousi | |
| 5,016,824 A | 5/1991 | Pietinen et al. | |
| 5,266,159 A | 11/1993 | Greenwood et al. | |
| 5,500,088 A | 3/1996 | Allison et al. | |
| 5,540,392 A | 7/1996 | Broderick et al. | |
| 5,544,757 A | 8/1996 | Geiger et al. | |
| 5,949,086 A | 9/1999 | Reponen et al. | |
| 5,960,104 A | 9/1999 | Conners et al. | |
| 6,122,065 A | 9/2000 | Gauthier | |
| 6,175,092 B1* | 1/2001 | Binette et al. | 209/587 |
| 6,199,463 B1 | 3/2001 | Quick | |
| 6,211,470 B1 | 4/2001 | Beran et al. | |
| 6,336,602 B1 | 1/2002 | Miles | |
| 6,398,914 B1 | 6/2002 | Furumoto | |
| 6,447,146 B1 | 9/2002 | Skinner et al. | |
| 6,466,305 B1 | 10/2002 | McBain | |
| 6,577,916 B1 | 6/2003 | Gehr et al. | |
| 6,752,165 B2 | 6/2004 | Johansson | |
| 6,778,936 B2 | 8/2004 | Johansson | |
| 6,846,381 B2 | 1/2005 | Jussila et al. | |
| 6,938,843 B2 | 9/2005 | Johansson | |
| 7,082,348 B1 | 7/2006 | Dahlquist et al. | |
| 7,085,615 B2 | 8/2006 | Persson et al. | |
| 7,130,040 B2 | 10/2006 | Lindgren et al. | |
| 7,240,863 B2 | 7/2007 | Ettaleb et al. | |
| 7,292,949 B2 | 11/2007 | Ding | |
| 7,381,303 B2 | 6/2008 | Sidhu et al. | |
| 7,778,786 B2* | 8/2010 | Ding | 702/81 |
| 2003/0009894 A1 | 1/2003 | Yamamoto | |
| 2003/0079544 A1 | 5/2003 | Floyd | |
| 2004/0025654 A1 | 2/2004 | Olsen | |
| 2005/0027482 A1* | 2/2005 | Benaoudia et al. | 702/183 |
| 2005/0103453 A1 | 5/2005 | Kankaanpaa | |
| 2005/0120840 A1 | 6/2005 | Koskovich | |
| 2005/0190958 A1 | 9/2005 | Woods et al. | |
| 2005/0263259 A1 | 12/2005 | Sidhu et al. | |
| 2006/0201582 A1 | 9/2006 | Edwards | |
| 2006/0278353 A1* | 12/2006 | Ding | 162/49 |
| 2006/0285336 A1 | 12/2006 | Davies | |
| 2007/0143066 A1 | 6/2007 | Floyd et al. | |
| 2007/0158040 A1 | 7/2007 | Benaoudia et al. | |
| 2007/0236680 A1 | 10/2007 | Barker | |
| 2008/0046209 A1* | 2/2008 | Ding | 702/81 |
| 2010/0121473 A1* | 5/2010 | Ding et al. | 700/104 |

OTHER PUBLICATIONS

Varhimo, A. et al. "Raw Materials" in Sundbolm, J. "Mechanical Pulping" Chapter 5, Fapet OY, 66-104 (1999).
Sum, S. T. et al. "Laser-excited Fluorescence Spectra of Eastern SPF Wood Species—An Optical Technique for Identification and Separation of Wood species", Wood Sci. Technol., 25, 1991, pp. 405-413.
Lawrence, A. H. "Rapid Characterization of Wood Species by Ion Mobility Spectrometry", Journal of Pulp and Paper Science, 15 (5), 1989, J196-J199.
Fuhr, B. J. "On-line Wood Species Sensor", Paper Age, Sep.-Oct. 2001, pp. 26-29.
Tyvaïnen "The Influence of Wood Properties on the Quality of TMP Made from Norway Spruce (*Picea abies*)—Wood from Old-growth Forests, First-thinnings, and Small Chips" 1995 International Mechanical Pulping Conference, pp. 23-34, 1995.
Dundar, E. et al. "Decreasing Specific Energy of Thermomechanical Pulps from Reduction of Raw Materials Variability", Sep. 2009, TAPPI Journal pp. 23-29.
Preikschat E. "Measuring the Moisture and Bulk Density of Pulp Wood Chips for Digester Control—with a Correction Algorithm for Frozen Conditions" Energy Conservation through Instrumentation, ISA Capital Cities Control Conference, May 13-15, 1980, pp. 33-38.
Allison et al "Dual adaptive control of chip refiner motor load" Pulp and Paper Canada, 96:3, T73-T79, 1995.
Berg et al "Deterministic consistency estimation in refining processes" Int. Mechanical Pulping Conference, Quevec, Canada, pp. 361-366, 2003.
Bergman "On-line chip analysis : new technology for an improved pulping process" Pulp and paper Canada, 99(12) pp. T453-T454, 1998.
Breck et al "Thermomechanical Pulping—a Preliminary Optimization", Transactions, Section technique, ACPPP, 13, pp. 89 95, 1975.
Brill "Effects of wood and chip quality on TMP properties" IMPC proceedings, Stockholm, pp. 153-162, 1985.
Cluett et al "Control and optimization of TMP refiners" Pulp and Paper Canada,96:5, T158-T162, 1995.
Ding et al "Improvement and Prediction of Kraft Pulp Yield Using a Wood Chip Quality Online Measurement System (CMSE)" Control Systems 2006.
Ding et al "Online Wood Chip Quality Measurement: Chip Density and Wood Species Variation" IMPC 2005.
Ding et al "Wood Chip Physical Quality Definition and Measurement" IMPC 2003.
Ding et al "Effects of some wood chip properties on pulp qualities" Pulp and Paper Annual Conference Proceedings, p. 35 , Jan. 29, 2003.
Ding et al "Economizing the Bleaching Agent Consumption by Controlling Wood Chip Brightness" Control Systems 2002.
Du et al "Nonlinear control of a wood chip refiner" Proceedings of the IEEE Conference on Control Applications. Albany, NY : IEEE. p. 1065 1066 , 1995.
Dumont et al "Wood chip refiner control" IEEE Control Syst. Mag. 8:2. 38 43 1988.
Eriksen et al "Consequences of Chip Quality for Process and Pulp Quality in TMP Production", International Conference, Mechanical Pulping, Oslo, Jun. 1981.
Evans et al "Refiner control effectively accomplished through adaptive control" Pulp & Paper Canada. 96:5. T163 T166, 1995.
Fisher et al "The interface between design and control. 1. Process controllability . 2. Process operability , 3. Selecting a set of controlled variables." Ind. Eng. Chem. Res. 27:597 615, 1988.
Fu et al "Chip refiner motor load adaptive control using a nonlinear Laguerre model" Second IEEE Conference on Control Applications. Vancouver, B. C. P. 371 376, 1993.
Fuglem et al "Influence of spruce properties on thermomechanical pulping Pilot scale result", International Mechanical Pulping Conference, Proceedings, 7582, 2003.
Hartler "Wood quality requirements in mechanical pulping" Nordic pulp and paper research journal, No. 1, pp. 4-10, 1996.
Hatton, "Chip quality monograph—Chapter 14 : Chip quality analytical procedures" Joint textbook committee of the paper industry pp. 303-323 (1999).
Hill et al "On the control of chip refining systems" Pulp and paper Canada , 94 (6), pp. T161-T165, 1993.
Hoekstra et al "The Effects of Chip Size on Mechanical Pulp Properties and Energy Consumption", International Conference, Mechanical Pulping, Washington, Jun. 1983.
Ingman "Utilization of Neural Network Technology for Some Pulp & Paper Industry Applications" 2000 Process Control, Electrical & Info. Conference Proceedings, 2000.
Jensen et al "Effect of Chip Quality on Pulp Quality and Energy Consumption in RMP Manufacture", Int symp. on fundamental concepts of refining, Appleton Wis., Sep. 1980.
Jones "Simulating the Development of pulp and Paper Properties in Mechanical Pulping Systems" Pulp and paper Can. 89(6): T214, 1988.
Jones "Simulation of the Performance of a TMP Mill" Pulp and paper Can. 91(2) : T81,1990.
Karrila et al "Review, Developments and Pulp and Paper Research Applications of Data Reduction with Neural Networks" Proceedings of TAPPI Paper Summit, Atlanta, GA, Mar. 4-6, 2002.
Kooi et al.,"Control of Wood Chip Refiner Using Neural Networks" TAPPI Journal, pp. 156 162, Jun. 1992.

Lama et al "Applying controllability techniques to analyze a white water network for improved productivity in integrated newsprint mills" Resources Conservation and Recycling, 37(3), p. 181-192, 2003.
Lama et al "Modeling the effect of plate age on the operation of TMP refiners" Conference Paper—Pulp and Paper Association PAPTAC, 2006.
Lama et al "Controllability analysis of a TMP newsprint refining process" Control Systems 2004 Conference, 2004; Pulp and Paper Canada, 107(10), 2006.
Lama et al "Analyzing the directionality of TMP Refining interactions" Tappi Journal, 2006.
Lama et al "A methodology to model TMP Newsprint refiners" Tappi Journal, 2006.
Lama et al (2006) "Optimal Operation of TMP-Newsprint Refiners" Nordic Pulp & Paper Research Journal, 21(4), p. 534-541, 2006.
Lama et al "An Empirical Model for Predicting Motor Load Changes Due to Plate Wear in TMP-Refiners" Nordic Pulp & Paper Research Journal, 21(4), p. 527-533, 2006.
Lama et al "Determining the inherent potential for specific energy reduction and variability attenuation in TMP-refining operations" Nordic pulp and paper research journal, 2007, vol. 22, No. , pp. 299-306.
Lanouette et al "Effect of Woodchips Characteristics on the Pulp and Paper Properties by the Use of PIs Analysis" EXFOR 2004.
Lanouette et al Amélioration de la Stabilité des Raffineurs et de la Qualité de Pâte par un suivi des copeaux << Les papetières du Québec, pp. 29-33, Dec. 2003.
Laperriere et al "Modeling and simulation of pulp and paper quality characteristics using neural networks" Tappi Journal , 84 (10), 59, 2001.
Laperriere et al "Chip Properties Analysis for Predicting Bleaching Agents Requirements" Tappi Fall Technical Conference, 2003.
Laperriere et al "Implementing Optimization with Process Simulation" Tappi Journal, vol. 1, No. 4, Jun. 2002.
Lecourt et al "Modeling TMP fibre morphology and pulp properties from wood and forest data: The example of Norway spruce significant" International Mechanical Pulping Conference , Proceedings , 67 75, 2003.
McQueen et al "Identification of a TMP wod chip refiner with implications for process control" Tappi journal, May 1999.
Marton et al "Energy Consumption in Thermomechanical Pulping", Tappi, 64 8, p. 71, 1981.
Miles "Refining intensity and pulp quality in high-consistency refining" Paperi ja Puu. 72:5. 508 514, 1990.
Miles et al "The flow of pulp in chip refiners" J. Pulp & Paper Sci. 16:2. J63 J72, 1990.
Miles et al "Refining intensity, energy consumption, and pulp quality in two stage chip refining" TAPPI J. 74:3. 221 230, 1991.
Miles et al. "Wood characteristics and energy consumption in refiner pulps", 1995.
Petersson et al "On line measurement of wood chip size" TAPPI J. 71(7), 78 81,1988.
Qian et al "Optimization of a wood chip refining process based on fuzzy relational models" Computers chem.. eng., vol. 21, pp. S1137-S1142, 1997.
Qian et al "Modeling of a Wood-Chip Refiner Using Artificial Neural Networks" Tappi journal vol. 78, No. 6, 1995.
Roche et al "A Practical approach to the control of TMP refiners" Proceedings of the '96 Control Systems Conference, Montréal, Canada : TAPPI Press. p. 129 135 ,1996.
Rogers et al "Automatic control of chip refining" Pulp & Paper Canada. 81:10. T277 T282, 1980.
Saltin et al "Improving the Reliability of Newsprint Quality Data Using Integrated Factor Networks for Paper Machine Control and Analysis", Engineering Conference Proceedings, Boston, pp. 55-61, 1992.
Saltin et al "Analysis and control of newsprint quality and paper machine operation using integrated factor networks: technique can help to identify source of quality changes" Pulp & paper Canada, CPPA. Technical Section. Control systems 1992 conference, Whistler BC, Canada, vol. 96, No. 7, pp. 48-51, Sep. 28, 1992.
Sarimveis et al H. , "Artificial Intelligence Tools for the On-Line Prediction of Quality Properties in Pulp and Paper Processes", Paper Summit, Atlanta, GA, 2002.
Sidhu et al "Advances in mechanical pulping control and measurement" Paptac 91st Annual Meeting , Montréal, Canada : PAPTAC. p. D751 D755 ,2005.
Sidhu et al "Modeling and Advanced Control of TMP Refiner System" Control System 2004, pp. 107-112, 2004.
Stationwala et al "Effect of feed rate on refining" J. Pulp & Paper Sci. 20:8. J236 J240, 1994.
Stationwala et al "The Effect on First Stage Refining Conditions on Pulp Properties and Energy Consumption" Journal of Pulp and Paper Science: vol. 19, No. 1, pp. J12 J18, Jan. 1992.
Strand "Quality control of high-consistency refiners" Tappi journal, Vo. 81, No. 12, 1998.
Strand et al "Optimum design, operation and control of mechanical pulping systems" International Mechanical Pulping Proceedings, Washington, D.C. TAPPI. p. 277 295, 1983.
Strand et al "Control and optimization of mechanical pulping systems" Tappi journal peer reviewed paper, 2000.
Strand "Factor Analysis as Applied to the Characterization of high yield Pulps" TAPPI 1987 Pulping Conference Proceedings, TAPPI Press, Atlanta, p. 61, 1987.
Strand et al. , "Millwide advanced quality control for the production of newsprint" IMPC conference, 2001.
Strand et al. "The Effect of production rate on specific energy consumption in high consistency chip refining" Proc. Intl. Mechanical Pulp Conf. Oslo, 1993.
Strand "Model based control of high consistency refining", TAPPI Journal, vol. 79(10), pp. 140-146, Oct. 1996
Strand et al "Control of Refiner Operation Using Integrated Factor Networks" 1992 Pulping Conference Proceedings, pp. 595-590, 1992.
Strand et al "Improving the Reliability of Pulp Quality Data trough Factor Analysis and Data Reconciliation" International pulp Conference, Helsinki, pp. 362-375, 1989.
Strand "The Effect of Refiner Variation on Pulp Quality" International mechanical pulping conference, pp. 125-130, 1995.
Strand et al "On-line Control and optimization of the refining process using a model based control system" International mechanical pulping conference, pp. 101-108, 1991.
Liimatainen et al. ."Mechanical pulping: Papermaking science and technology series; Chapter 5 : Grinding and pressure grinding" SUNDHOLM vol. 5, Finland : Finnish Paper Engineers' Association and TAPPI, pp. 107-156, 2000.
Tyrväinen "The influence of wood properties on quality of TMP made from Norway spruce (*Picea abies*)—Wood from old-growth forests, first-thinnings, and small chips" 1995 International mechanical pulping conference, pp. 23-34, 1995.
Wood "Chip Quality Effects in Mechanical Pulping ; A Selected Review" 1996 Pulping Conference, pp. 491-497.
Zhu et al "A neural Network for Modeling Pulp Process" Pulp and Paper Canada, 98:9, pp. T298-T301, 1997.
Miles et al "Wood quality and energy consumption in the production of refiner pulps", 1994 TAPPI Pulping Conference, Proceedings, 401-425, 1994.
Myllyneva, J. et al. "Fuzzy Control of Thermomechanical Pulping", Proceedings of IMPC 1991, Minneapolis, MN, pp. 381-384.
Mosbye, K., et al. "Use of refining Zone Temperature Measurements for Refiner Control", Proceedings of IMPC 2001, Helsinki, Finland, Jun. 2001.

\* cited by examiner

METHOD AND SYSTEM FOR STABILIZING DRY-BASED DENSITY OF WOOD CHIPS TO BE FED TO A CHIP REFINING PROCESS

FIELD OF THE INVENTION

The present invention relates to the field of refining process automation for the production of wood-based products, and more particularly to methods and systems for stabilizing wood chip refining processes.

BACKGROUND OF THE INVENTION

Wood chips being one of the main raw materials entering into pulp production processes such as thermomechanical pulping (TMP), chemical-thermomecanical pulping (TCMP) or mechanical pulping (MP) processes, or into production processes of other wood-based products such as fibreboards (MDF, HDF) variations in their physical properties have a direct impact on process control performance as well as on final product qualities. In the particular case of a TMP process, the quality of wood chips being fed to the refiners is of a great importance, since it is known to affect the refining process. It is well known that a typical TMP process is characterized by three critical operational variables, namely specific energy, production rate and consistency. For a given process design, specific energy consumption is the parameter that correlates most strongly to evolving pulp properties, as explained by Mosbye, K., et al. in "Use of Refining Zone Temperature Measurements for Refiner Control", *Proceedings of IMPC* 2001, Helsinki, Finland, June 2001. While specific energy can in theory be kept constant through adjustments to motor load or production rate, in practice the absence of on-line data about dry wood chip/fibre volume and moisture content means that the control of this variable will be subjected to instability, as mentioned by Cluett, W. R., et al. in "Control and Optimization of TMP Refiners", *Pulp & Paper Canada*, 96:5 (1995) pp. 31-35. The production rate, which is directly affected by the quantity of dry fibre refined, has a major impact on both energy consumption and pulp properties. The dilution water flow rate depends on chip moisture content and the consistency target as stated by Myllyneva, J. et al. in the above-mentioned reference. Consistency variations during normal operation are at least 4-6% and even higher, as reported by Hill, J., et al. in "On the Control of Chip Refining Systems", *Pulp & Paper Canada*, 94:6 (1993), pp. 43-47. Generally, known TMP process control strategies work according to the hypothesis that wood chip qualities are stable. Any variation in chip quality will be considered as a disturbance in process control. In fact, chip quality changes quite rapidly, and known control strategies cannot efficiently eliminate its influence, which prompts fluctuations of the three operational variables of the refining process mentioned above. Wood species variation is an important factor that can negatively impact pulp quality.

A system for measuring optical reflection characteristics of chips such as brightness, along with other important chip properties, such as moisture content, which is commercially known as the Chip Management System (CMS), is described in U.S. Pat. Nos. 6,175,092 B1 and 7,292,949 B2 (US 2005/0027482) both issued to the present assignee. Some pulp mills have used such system to manage their chip piles according to chip quality, as discussed by Ding et al. in "Economizing the Bleaching Agent Consumption by Controlling Wood Chip Brightness" *Control System* 2002 *Proceedings*, Jun. 3-5, 2002, Stockholm, Sweden, pp. 205-209. Chip quality assessment can be defined as the synthesis of measurements made of chip physical characteristics, as explained by Ding et al. in "Effects of Some Wood Chip Properties on Pulp Qualities" 89$^{th}$ Pulp and Paper Annual Conference Proceedings, Jan. 29, 2003, p. 35. Ultimately, this definition depends on the importance of each chip characteristic for a given process. Continuous variations in wood basic density and moisture content occurring in chip flow tend to cause variations in refining consistency, which in turn affect pulp uniformity and energy consumption as reported in U.S. Pat. No. 7,292,949 B2 and by Ding et al. in " Wood Chip Physical Quality Definition and Measurement", 2003 *International Mechanical Pulping Conference*, Quebec City, Canada, Jun. 2-5 2003, pp. 367-373 in view of Tyväinen "The Influence of Wood Properties on the Quality of TMP Made from Norway Spruce (*Picea abies*)—Wood from Old-growth Forests, First-thinnings, and Small Chips" 1995 International Mechanical Pulping Conference, pp. 23-34, 1995.

In pulp mills, visual evaluation of wood chip quality is widely used. From the chip color, a specialist can determine the chip species and estimate freshness, bark, rot, and knot contents. A known approach consists of sorting trees according to their species or blend of species prior to wood chips manufacturing, to produce corresponding batches of wood chips presenting desired characteristics associated with these species. Typically, hardwood trees such as poplar, birch and maple are known to generally produce pale wood chips while conifers such as pine, fir and spruce are known to generally yield darker wood chips. In practice, wood chips batches can either be produced from trees of a same species or from a blend of wood chips made from trees of plural species, preferably of a common category, i.e., hardwood trees or conifers, to seek wood chips uniformity.

Many studies have shown that wood species and dry-based density are the dominant factors in pulping performance and pulp quality. The spruce family is the most favorable species for TMP as mentioned by Varhimo, A. et al, in "Raw Materials" in Sundbolm, J. "Mechanical Pulping" Chapter 5, Fapet OY, 66-104 (1999). Although chip aging can be observed from chip brightness, it is only useful for substantially unvaried wood species. When an unknown proportion of wood species is present, more information is needed to provide reliable chip quality assessment. Basic density is one of the most studied wood properties, and it varies substantially between and within various wood species. Basic density is not, however, an independent property but is determined by several characteristics of wood. As also mentioned by Varhimo et al, variations in wood basic density result in pulp quality variations. There is a good correlation between basic density and dry bulk density, the chip flow usually is metered by volume, and dry bulk density variations will cause fluctuations in the production rate, as reported by Dundar, E. et al, in "Decreasing Specific Energy of Thermomechanical Pulps from Reduction of Raw Materials Variability", September 2009, TAPPI Journal pp. 23-29.

For the purpose of wood dry-based density measurement, a sampling system used to determine moisture content and bulk density is proposed by Preikschat E. in "Measuring the Moisture and Bulk Density of Pulp Wood Chips for Digester Control—with a Correction Algorithm for Frozen Conditions" Energy Conservation through Instrumentation, ISA Capital Cities Control Conference, May 13-15, 1980, pp. 33-38. This sampling system has been suggested for a white liquor flow rate control of a Kraft process. A height measurement apparatus for determining the volume/density of wood chips on a conveyor is also proposed by Beran et al. in U.S. Pat. No. 6,211,470 B1, where the bone dry bulk density can be measured and used for a Kraft process control. Another sampling system to be used to measure bulk density for digester control is proposed by Bäcklund in European Patent no. 738 342 B1. In this system, the moisture content is estimated from information on the chip weight volume and wood basic density. U.S. Pat. No. 6,447,639 B1 to Warren et al teaches a process for controlling a digester using real time measurement of moisture content and species of wood, without density measurement.

For the purpose of wood species identification, some optical testing methods are proposed by Sum, S. T. et al. in "Laser-excited Fluorescence Spectra of Eastern SPF Wood Species—An Optical Technique for Identification and Separation of Wood species", *Wood Sci. Technol.*, 25, 1991, pp. 405-413., and by Lawrence, A. H. in "Rapid Characterization of Wood Species by Ion Mobility Spectrometry", *Journal of Pulp and Paper Science*, 15 (5), 1989, J196-J199, and a chemical vapor analysis is proposed by Fuhr, B. J. IN "On-line Wood Species Sensor", *Paper Age*, September-October 2001, pp. 26-29. These known methods have been applied either off-line in laboratory or on-line for monitoring a specific wood species. However, these techniques cannot be used to evaluate a mixture involving more than two wood species. An on-line measurement system such as described in US 2005/0027482 and Ding et al. cited above, can produce data that is useful for identifying the proportion of pure wood species making up a mixture of wood chips, on the basis of optical reflection and moisture measurements made on wood chips. For example, the brightness of Balsam Fir is quite similar to that of Black Spruce, but Fir's moisture content is about 55%, while Spruce moisture content is about 40%. Likewise, although Jack Pine's moisture content is similar to that of Black Spruce, Pine is the darker species of the two. For a mixture of more than two species, it is possible to estimate a breakdown of the species present. US 2005/0027482 teaches the use of an estimation model based on a feed-forward neural network that is built from optical reflection-based measurements, namely R,G,B,H,S,L, and dark chip content (D), along with moisture measurement as input variables, in which chip freshness (ageing) and species are controlled, and the selection of the input variables for the FFNN has been performed using known Principal Component Analysis (PCA) technique from the trials results. The well known Levenberg-Marquardt algorithm has been used to train the model, to provide at an output thereof an indication of wood species composition, usually representing the purity level of a main species forming a chip sample. However, it has been observed that such approach provides an estimation of the proportion of each species within a range of only about ±10%, which is generally insufficient to allow an efficient control over species variation in wood chips fed to the pulping process. Although US 2005/0027482 teaches that chip quality on-line measurement is very useful for stabilizing chip input, and that feedback information can control chip-feeding screws so as to take suitable proportions of chips from different piles or silos, such approach is not efficient to minimize specific energy. The system described in US 2005/0027482 for measuring chip moisture content and wood species does not involve any chip density measurements.

In prior published application no. US 2006/0278353 also naming the present assignee, there is disclosed the use of a measurement system for estimating and controlling relative proportion of wood chips originating from a plurality of sources characterized by various wood species, in a mass of wood chips to be fed to a process for producing pulp, wherein light reflection-related and density-related properties are used as input in a model characterizing a relation between such wood chip properties and species information. This principle allows efficient monitoring of the variation in wood species composition characterizing the wood chips to be processed, for the purpose of stabilizing chip feeding control and optimizing process parameters adjustment. When installed in the chip feeding process, the measurement system generates on-line chip characteristics information that can be used to control the mixture of chips from the different piles in order to stabilize the dry mass of wood chips entering the digester stage of a Kraft process.

As opposed to chemical processes involving digesters, pulp production processes such as TMP, CTMP or MP generally use, upstream the refining process, processing stages of retention, atmospheric presteaming, washing/dewatering, preheating and/or impregnation (CTMP), etc. Similarly, production processes of wood-based products such as MDF or HDF generally use, upstream the refining process, processing stages of retention and preheating/steaming. Due to these upstream processing stages, the known, direct chip feeding control approaches used in chemical processes involving digesters cannot be used to efficiently stabilize the refining process.

SUMMARY OF THE INVENTION

It is a main object of the present invention to provide improved methods and systems for stabilizing wood chip refining processes.

According to the above-mentioned main object, from a broad aspect of the present invention, there is provided a method for stabilizing dry-based density of wood chips to be fed to a chip processing stage upstream of a chip refining process from a plurality of independently discharging sources of wood chips being characterized by one of a pure wood species and a mixture of wood species. The method comprises the steps of: i) estimating on-line a set of wood chip properties characterizing the wood chips to generate corresponding wood chip properties data, said set including at least one light reflection-related property, moisture content and dry-based density; ii) feeding the wood chip properties data at corresponding inputs of a reference model capable of comparing the estimated dry-based density with a predetermined target to produce error data, and selectively modifying discharge rate set points of one or more of the wood chip sources to minimize the error data within fluctuation limits around the target; iii) controlling the discharge rates of the wood chip sources in accordance with the set points to substantially stabilize the dry-based density of the wood chips.

According to the same main object, from another broad aspect, there is provided a method for feeding wood chips at a substantially stable dry-based density to a processing stage upstream of a chip refining process from a plurality of independently discharging sources of wood chips being characterized by one of a pure wood species and a mixture of wood species. The method comprises the steps of: i) estimating on-line a set of wood chip properties characterizing the wood chips to generate corresponding wood chip properties data, said set including at least one light reflection-related property, moisture content and dry-based density; ii) feeding the wood chip properties data at corresponding inputs of a reference model capable of comparing the estimated dry-based density with a predetermined target to produce error data, and selectively modifying discharge rate set points of one or more of the wood chip sources to minimize the error data within fluctuation limits around the target; and iii) controlling the discharge rates of the wood chip sources in accordance with the set points to feed the processing stage with the wood chips at said substantially stable dry-based density.

According to the same main object, from a further broad aspect, there is provided a system for stabilizing dry-based density of wood chips to be fed to a processing stage upstream of a chip refining process from a plurality of independently discharging sources of wood chips being characterized by one of a pure wood species and a mixture of wood species. The system comprises illumination means for directing light onto an area of said wood chips, the illuminated wood chips area presenting light reflection characteristics being substantially representative of all said wood chips, an optical imaging device for sensing light reflected from the illuminated wood chips area to produce image data representing at least one light reflection-related property characterizing the wood chips, a moisture sensor for generating data representing moisture content of the wood chips, a volume meter for generating data representing volume of the wood chips; and a weighing device for generating data representing wet weight of the wood chips. The system further comprises a data processing unit programmed to generate data representing dry-based density of the wood chips from the moisture content data, the volume data and the wet weight data, and further programmed with a reference model receiving at corresponding inputs thereof the image data, the moisture content data and the dry-based density data, for comparing the dry-based density with a predetermined target to produce error data, and for selectively modifying discharge rate set points of one or more of the wood chip sources to minimize the error data within fluctuation limits around the target, and a control unit operatively connected to the discharging sources for controlling the discharge rates thereof in accordance with the set points to substantially stabilize the dry-based density of the wood chips.

According to the same main object, from another broad aspect, there is provided a system for feeding wood chips at a substantially stable dry-based density to a processing stage upstream of a chip refining process from a plurality of independently discharging sources of wood chips being characterized by one of a pure wood species and a mixture of wood species. The system comprises illumination means for directing light onto an area of said wood chips, said illuminated wood chips area presenting light reflection characteristics being substantially representative of all said wood chips, an optical imaging device for sensing light reflected from the illuminated wood chips area to produce image data representing at least one light reflection-related property characterizing the wood chips, a moisture sensor for generating data representing moisture content of the wood chips, a volume meter for generating data representing volume of the wood chips, and a weighing device for generating data representing wet weight of the wood chips. The system further comprises a data processing unit programmed to generate data representing dry-based density of the wood chips from the moisture content data, the volume data and the wet weight data, and further programmed with a reference model receiving at corresponding inputs thereof the image data, the moisture content data and the dry-based density data, for comparing the dry-based density with a predetermined target to produce error data, and for selectively modifying discharge rate set points of one or more of the wood chip sources to minimize the error data within fluctuation limits around the target, and a control unit operatively connected to the discharging sources for controlling the discharge rates thereof in accordance with the set points to feed the processing stage with the wood chips at said substantially stable dry-based density.

BRIEF DESCRIPTION OF THE DRAWINGS

Preferred embodiments of the present invention will now be described in detail with reference to the accompanying drawings in which.

DETAILED DESCRIPTION OF THE PREFERRED EMBODIMENTS

Basically, according to the present invention, It has been discovered that, where a chip processing stage upstream of a chip refining process is involved, dry-based density data, moisture content and one or more light reflection-related properties can be used by a reference model for selectively modifying the discharge rate set points of one or more of the wood chip sources, to provide substantial stabilization of the dry-based density of the wood chips around a predetermined target.

Figure 1:
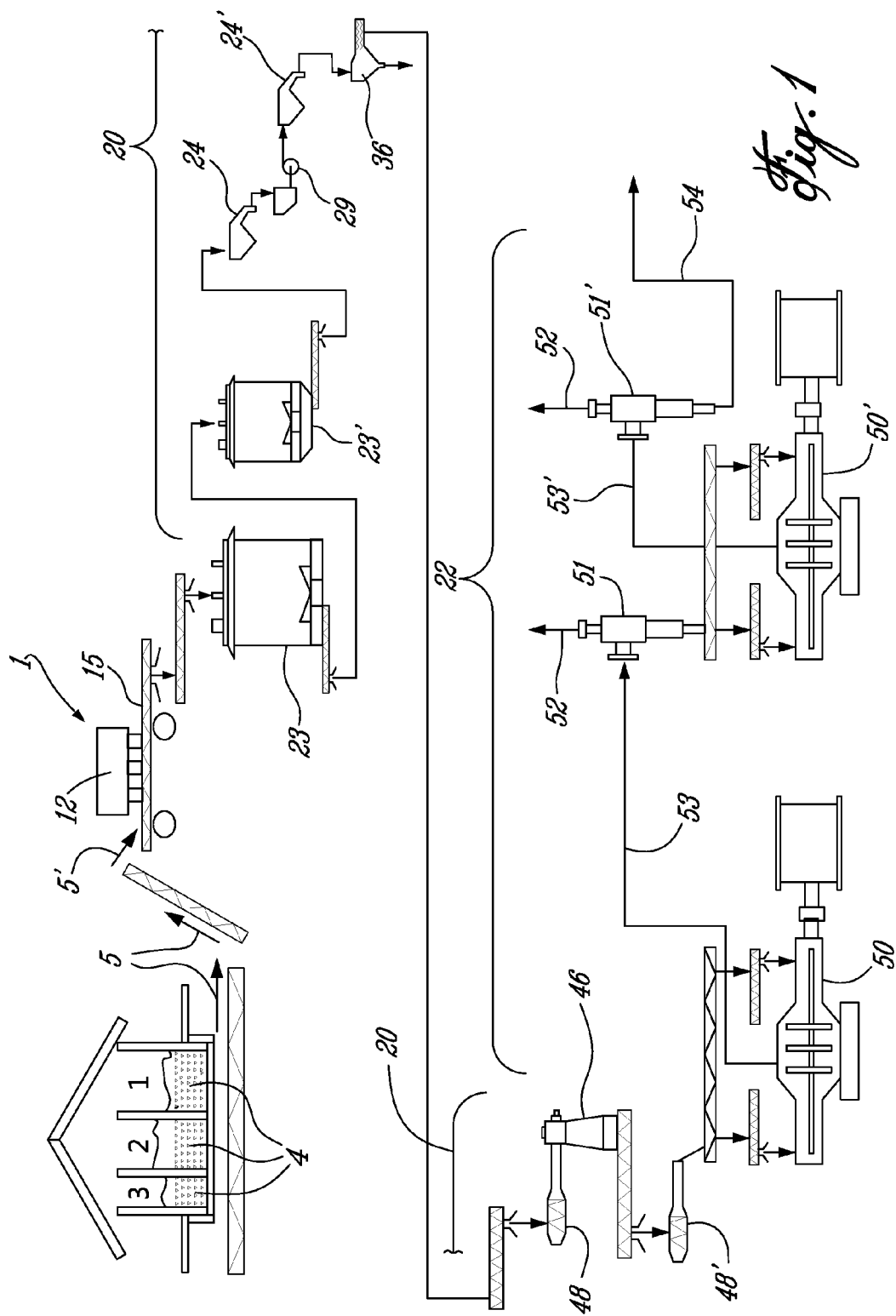
FIG. 1 is a schematic diagram of an example of TMP processing stage upstream a refining process making use of a system for stabilizing dry-based density of wood chips.
Figure 1A:
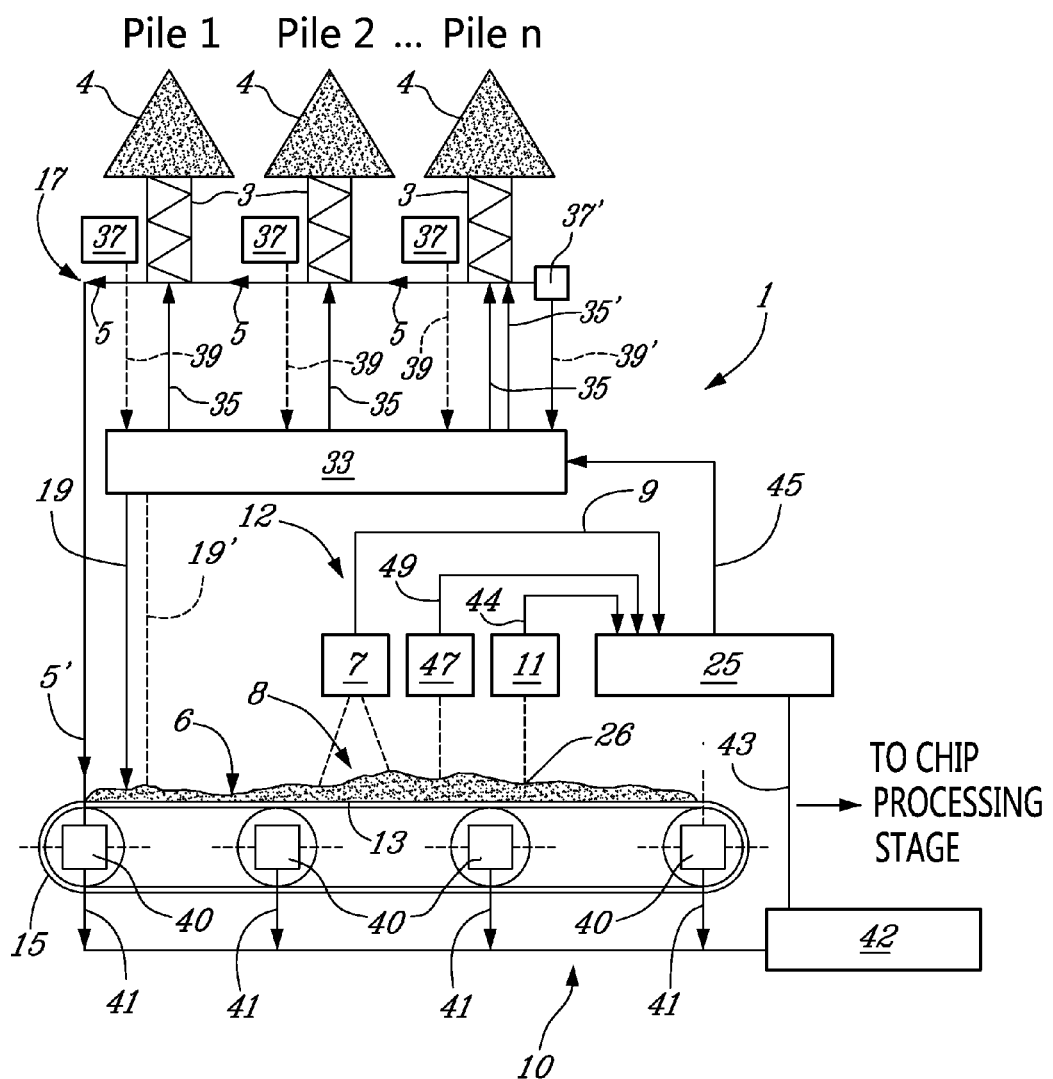
FIG. 1A is a schematic diagram of the system of FIG. 1, using a control unit operatively connected to wood chip discharging sources for controlling the discharge rates thereof to substantially stabilize the dry-based density of the wood chips.
Figure 2:
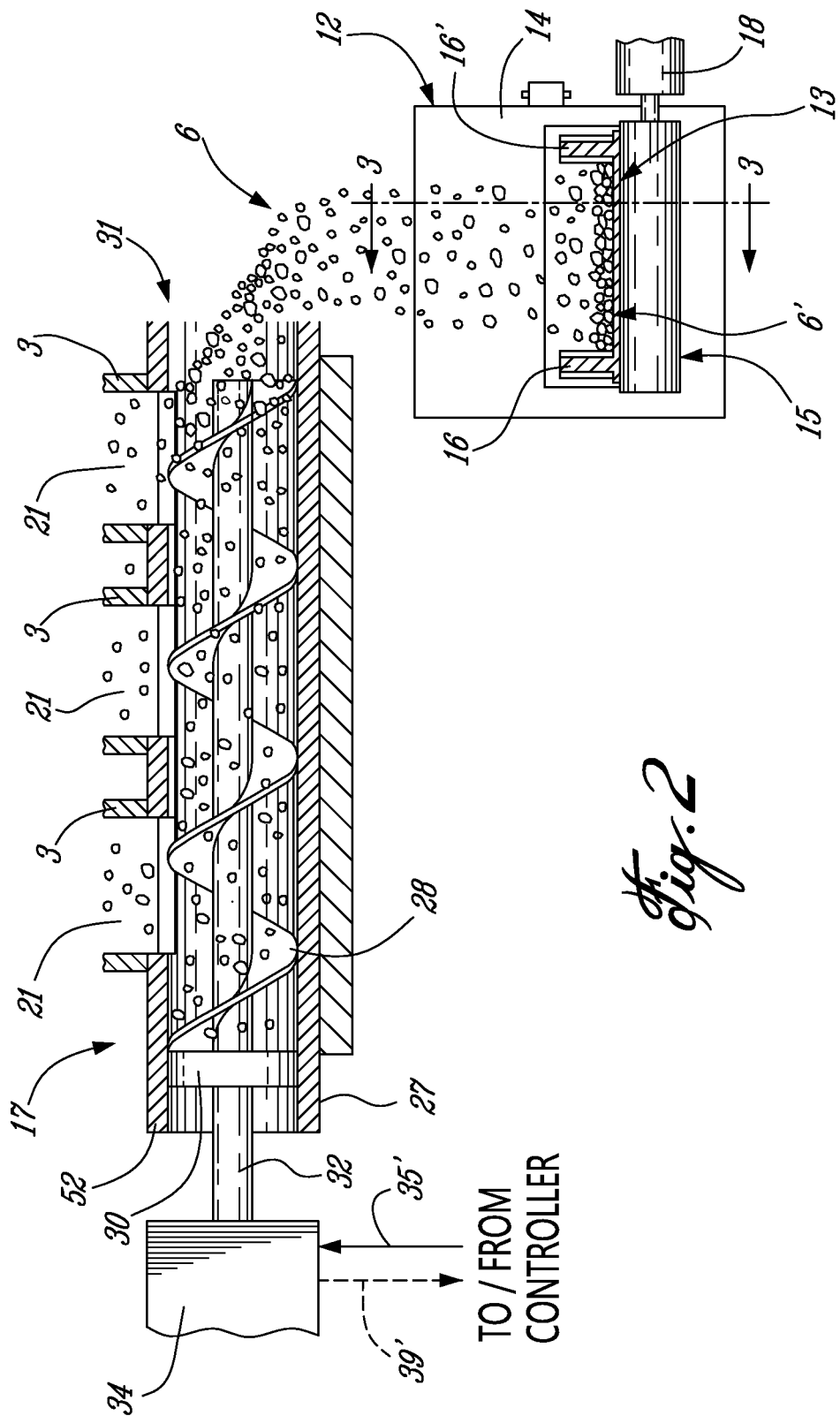
FIG. 2 is a partially cross-sectional end view of a main discharging screw device feeding a conveyor transporting the wood chips through the optical, moisture and volume measurement station as part of the system of FIG. 1A.

Referring now to FIG. 1 in view of FIG. 1A, there is generally represented at 1 a system for stabilizing dry-based density of wood chips originating from a plurality of sources of wood chips numbered 1 to n (n=3 in the example shown), usually in the form of piles of raw wood chips 4, in communication with means for discharging such as screw devices 3 as shown on FIG. 1A, the output of which being received and transported by a main discharging screw device 17 also represented by a series of arrows 5, which screw device will be described below in detail with reference to FIG. 2. As will be also explained below in detail, the wood chips 4 of each pile may be characterized by either a substantially pure wood species or a mixture of wood species of variable quality, depending upon available chips from providers. For example, a first source (Silo 1) can be composed mostly of spruce as a main ingredient in the process, a second source (Silo 2) can be composed of jack pine or balsam fir depending on the season, and a third source (Silo 3) can be composed largely of hardwood. The main screw device 17 discharges the wood chips as indicated by arrow 5' to form a mass of blended wood chips 6 transported by a screw or conveyer 15, to be fed to a chip processing stage as generally indicated at 20, which is upstream of a chip refining process carried out by a refining stage generally indicated at 22. For a typical TMP process, the chip processing stage generally makes use of one or more retention silos 23, 23', of one or more washing units 24, 24' in communication through a pump 29, followed by a dewatering unit 36. Optionally, an atmospheric presteaming unit (not shown) may be provided between retention silo 23' and washing unit 24. The chip processing stage can be also provided with a preheating unit 46 fed by compressed chips through a first plug-screw feeder 48, at the output of which unit 46 a second plug-screw feeder 48' can be provided to feed with processed chips the refining stage 22. In the case of a CTMP process, an impregnation unit for chemically processing the chips prior to the refining stage 22 can be used. For a typical production process of wood-based products such as MDF or HDF, the processing stage generally only makes use of retention silos and preheating unit. The refining stage 22 shown in the example of FIG. 1 includes primary and secondary refiners 50, 50' connected in series through line 53 and a first cyclone 51 for separating the partially refined pulp from the process steam, which is directed as indicated by arrow 52 to a heat recovery unit (not shown). For a same purpose, a second cyclone 51' receives through line 53' the steamed pulp coming from secondary refiner 50', for producing at output line 54 the fully refined pulp. It is to be understood that a single one or more than two refiners can also be used.

Referring again to FIG. 1A, the system 1 includes a measurement station generally designated at 12 including an optical scanning unit 7 integrating illumination means for directing light onto a scanned area 8 of wood chips 6, and an optical imaging device for sensing light reflected from the illuminated wood chips, to produce through output line 9 image data representing at least one light reflection-related property characterizing the wood chips 6. Although only wood chips forming the top surface of the mass of wood chips 6 are illuminated and sensed, the scanning mode of operation of unit 7 ensures that these illuminated wood chips present light reflection characteristics substantially representative of all wood chips 6. The measurement station 12 further includes a density measuring unit preferably making use of a weighing unit generally designated at 10 for measuring weight of at least a representative portion of the wood chips 6, and of a volume meter 11 for measuring volume of the same portion of wood chips. The weighing device 10 preferably makes use of a plurality of weight sensors such as load cells 40 transversely mounted in pairs along wood chip conveyer 15 and mechanically coupled to the endless belt 13 thereof to be responsive to the wet weight of wood chips transported by conveyer 15. The wet weight signals generated by load cells 40 through respective output lines 41 are combined by a weighing acquisition module 42 that produce resulting calibrated and balanced weight data. A weighing device such as Z-Block from BLH Electronics Inc. Canton, MA, can be used. A load cell is a transducer that converts force into a measurable electrical output. Each load cell included bonded strain gauges, which are positioned so as to measure applied shear stresses. The strain gauges are wired to a Wheatstone bridge circuit which, when crossed with an excitation voltage, produces changes in the electrical output that are proportional to the applied force. Thanks to low deflection, low mass design and the absence of moving parts, such load cells afford excellent high frequency response for dynamic force measurement. Three measurements are considered for on-line chip weighing, namely: wood chip weight, speed of belt 13 through line 19' and position of main discharging screw device 17 through line 39'. A check was performed on the precision of the load cells 40. While the conveyer was running, a standard 25-kilogram weight was placed on each load cell 40. The results are shown in Table 1.

TABLE 1

| Test No. | $W_{Standard}$ (kg) | $W_{Measurement}$ (kg) Minimum | Maximum |
|---|---|---|---|
| 1 | 0 | −0.2 | 0 |
| 2 | 25 | 24.9 | 25.1 |
| 3 | 50 | 49.8 | 50.2 |
| 4 | 75 | 74.9 | 75.1 |
| 5 | 100 | 99.7 | 100.2 |
| 6 | 125 | 124.7 | 125.5 |
| 7 | 150 | 149.2 | 150.0 |
| 8 | 175 | 174.5 | 175.2 |
| 9 | 200 | 199.8 | 200.2 |

It is to be understood that any other suitable weighing device based on a different weight measurement principle may be used.

The volume meter 11 is preferably based on an optical profile sensor model Ruler E120 from SICK IVP AB (Sweden) which measures the profile of wood chips 6. Ruler E120 is a high-speed data streamer for true shape measurement of objects. The camera delivers calibrated 3D profiles of objects passing through the measurement region, from which data volume measurement can be readily derived. It is to be understood that any other suitable profile sensor or distance ranging device based on a different measurement principle, or any other sensor adapted to derive volume measurement, may be used. Weight and volume measurement data generated through output lines 43 and 44 respectively, are used to derive data representing dry-based density characterizing the mass of wood chips 6, expressed as basic density and/or dry bulk density, as will be explained below in more detail. In order to provide a more accurate estimation, the set of wood chip properties further includes moisture content, which property is preferably measured by a moisture sensor 47 provided on the measurement station 12, producing through output line 49 data representative of the moisture content of the wood chip 6. The system 1 further includes a data processor unit 25 being programmed to generate the data representing dry-based density of the wood chips from the moisture content data, the volume data and the wet weight data. The data processor unit 25 is further programmed with a reference model receiving at corresponding inputs thereof the image data, the moisture content data and the dry-based density data, for comparing the dry-based density with a predetermined target to produce error data. The reference model is thus capable of selectively modifying the discharge rate set points of one or more of the wood chip sources (piles) to minimize the error data within fluctuation limits around the target. Information about the modified discharge rate set points is sent through control output line 45 to a controller unit 33 operatively connected to the drive motor (not shown) provided on each discharging screw device 3 through control lines 35 for selectively modifying the discharge rate of one or more of the wood chip sources or piles 1 to n, according to the current values of the set points, to substantially stabilize the dry-based density of the wood chips fed to the processing stage. Appropriate reference models will be described below in detail. The controller unit 33 is also connected to the drive motor of the main discharging screw device 17 through further control line 35', as will be explained below with reference to FIGS. 2 and 3. To obtain better control accuracy over the discharge adjustment, a volumetric sensor 37 is coupled to each screw device 3 to provide through feedback lines 39 a signal indicating of the effective discharge rate as a result of commands received from controller 33. A similar sensor 37' is coupled to the main discharging screw device to provide feedback signal to controller 33 through line 39'. Conveniently, a conventional encoder mechanically or optically coupled to the driving shaft of each screw device can be used as volumetric sensor.

As to the weighing function of the system, the disturbance due to the fact that wood chips are falling on the conveyer belt 13 under gravity will now be defined and analysed. As shown on FIG. 2, wood chips 6 fall from a given height of typically about one meter onto belt 13 of conveyer 15. The chip's gravitational potential energy is equal to its weight times the falling distance. It is desirable to model this gravity force in order to make an assessment of a possible source of measurement error. For a given period of time, the chips fall on an area covering about $0.31 \times 1.5$ m$^2$ in the present example. Supposing that the average wood chip thickness is 5 mm, fallen chip volume is about:

$$V = 0.31 \times 1.5 \times 0.005 = 2.325 \times 10^{-3} \, (m^3) \quad (1)$$

Assuming an average basic density ρ of wood chip is 450 kg/m$^3$, the fallen chip mass is:

$$m = \rho \times V = 450 \times 2.325 \times 10^{-3} = 1.04625 \, (kg) \quad (2)$$

the chip's gravitational potential energy is:

$$E_C = m \times g \times h = 1.04625 \times 9.81 \times 1 = 10.26 \, (N.m) \quad (3)$$

wherein:
g=acceleration of gravity=9.81 (m/s$^2$)
h=chip falling height (m)
The idler reaction work is:

$$W = F \times L \quad (4)$$

Wherein:
F=idler reaction force (N),
L=conveyer length (m).
According to the energy conservation law, the chip's gravitational potential energy equals the idler reaction work ($E_C=W$). Thus, by transferring values between equations (3) and (4):

$$F = E_C/L = 10.2637/17 = 0.60 \, N = 61.18 \, (g) \quad (5)$$

Taking into account equation (5), the chip gravity force equals idler reaction force F, and is equivalent to 61.18 (g). In practice, this force generally does not really influence measurement accuracy, as the typical analog/digital resolution of instrumentation used is about 9 (g) and its probable analog/digital system absolute error is 300 (g).

A method used by the weighing unit and computer to derive wood chips mass and density measurements will now be explained in view of the following parameters and corresponding definitions:
Wet Chip Mass Modified:

$$m_m = m_c = C_g \frac{h_{fall}}{L} \, (kg)$$

Chip Unit Length Mass:

$$m_l = \frac{m_m}{l_c} \, (kg/m)$$

Belt Feed Forward Length: $l_f = v_b \times t$ (m)
Chip Fall Mass: $m_d = m_l \times l_f$ (kg)
Fall Volume: $V_d = l_f \times A_s$ (m$^3$)
Fall Bulk Density:

$$\rho_{bulk\_d} = \frac{m_d}{V_d} \times C_{bulk} \, (kg/m^3)$$

Fall Basic Density:

$$\rho_{basic\_d} = \frac{m_{dry\_d}}{V_d} \times C_{basic} \, (kg/m^3)$$

Dry chip mass: $m_{dry\_d} = m_d(1-H_m)$
Chip Flow Profile: $A_s$(m$^2$)
Measured parameters are:
Belt speed: $v_b$ (m/s)
Chip Covered Length on Belt: $l_c$ (m)
Wet Chip Mass Measured: $m_c$ (kg)
Global Moisture Content: $H_m$ (%)
Height of CMS to Chip Bed: $h_c$ (m)
Exemplary chip feeding configuration parameter values are:
Chip Passage Width: $l_p$=0.31 (m)
Height of CMS to Belt: $h_{CMS}$=0.18 (m)
Chip Fall Height: $h_{fall}$=1 (m)
Gravity Acceleration: g=9.81 (m/s$^2$)
Conveyer Length L=16.7 (m)
Coefficients and exemplary set values are:
Chip Nominal Mass that Hits the Belt: $C_g$=0
Chip Flow Profile Correction Coefficient: $C_{pc}$=1
Chip Bulk Density Correction Coefficient: $C_{bulk}$=1
Chip Basic Density Correction Coefficient: $C_{basic}$=1

For an on-line chip weigh measurement, the desired outputs are chip moisture content or weight, dry weight, bulk density and basic density. On-line chip volume data being required to calculate chip densities, a profile sensor is used to measure chip bed profile as mentioned before. Chip dry mass as well as bulk and basic densities can be calculated by using chip moisture content, chip volume and the on-line chip wet mass measurement. For the purpose of experimentation, oversized and undersized chips were screened out before entering the conveyor, thus making it possible to establish a solid correlation between basic density and bulk density.

Let's assume that load cell sampling frequency is 1/t, where t is a time interval between two samples. Belt speed is v, and the mass of chips covering the length of the conveyor is l, a variable that will depend on the position of the chip unloading screw. For a given time, k, the chip mass falling onto the belt can be calculated as:

$$m_d(k) = \frac{m_m(k)}{l_c(k)} \times v_b(k) \times t(k) \qquad (6)$$

For a given start time $t_0$ to end time $t_{end}$, the total chip mass measured can be expressed as:

$$m_{total} = \sum_{k=t_0}^{t_{end}} m_d(k) \text{ where: } k = t_0, t_1, \ldots t_{end} \qquad (7)$$

Figure 6:
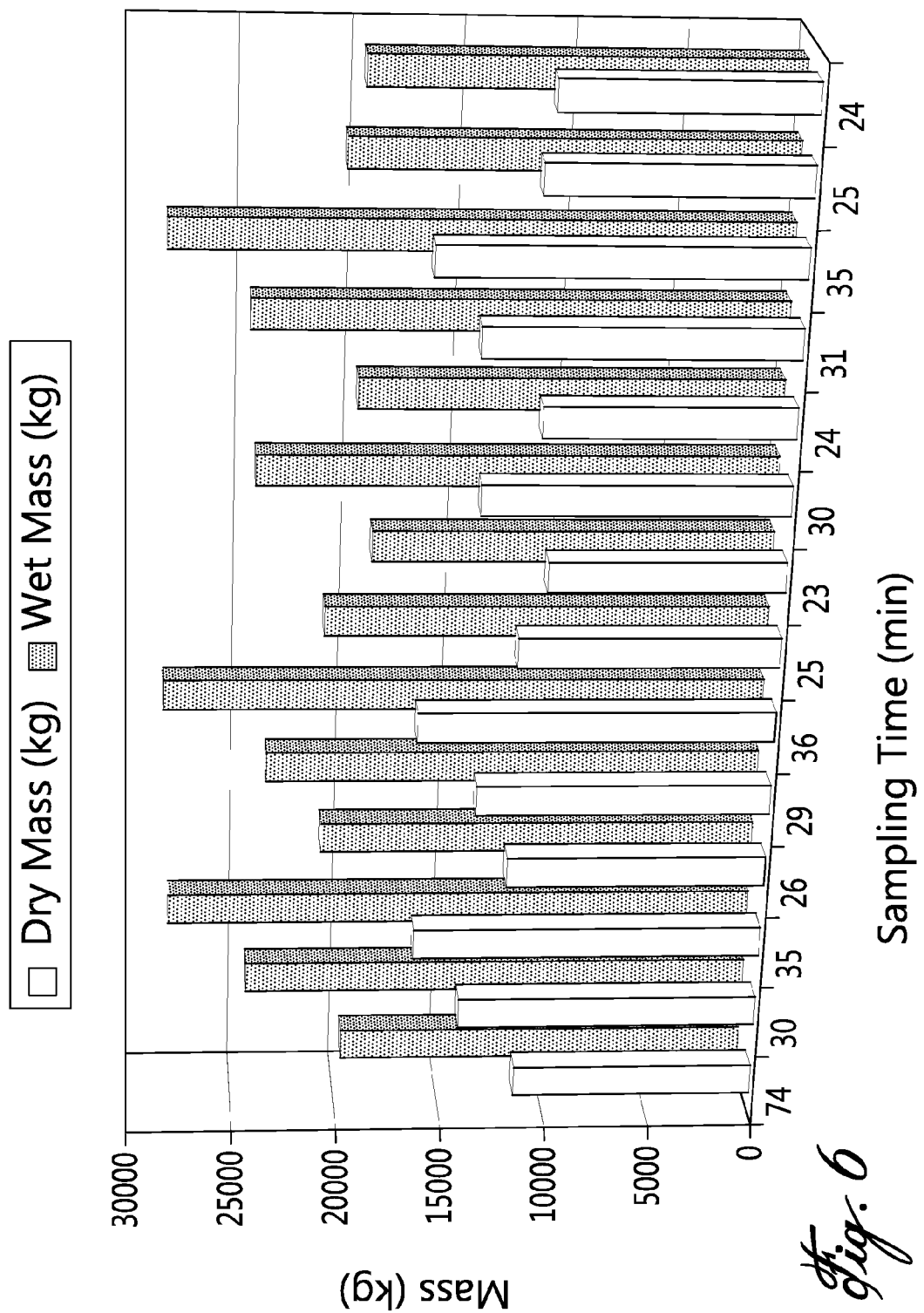
FIG. 6 is a bar graph showing the results of on-line measurement of the mass of wood chips fed to the measurement station.

However, the wood chip mass being generally not homogeneously distributed over the belt, an error will appear in the equation (7). This error can be eliminated if the conveyor 15 is empty at the start of sampling time $t_0$, and the main discharging screw device 17 is stopped at end of sampling time $t_{end}$. The measurement will be halted once and there are no longer any chips on the conveyor. As mentioned above, important variables for evaluating chip basic density and wood chip species variation are the values derived from chip wet mass and dry mass measurement. With the measurement station used in the example described above, the accuracy of load cells is better than ±0.5%. Test results are shown on FIG. 6. A validation test was performed in a TMP mill, in which, for a given volume of dry chips corresponding to 299.4 (t), the measurement station used gave a figure of approximately 290.3 (t), a result which reflects the fact that some lost, unrecoverable chips were not accounted for during the feeding stage.

The measurement station 12 is preferably based on the wood chip optical inspection apparatus known as CMS-100 chip management system commercially available from the Assignee Centre de Recherche Industrielle du Quebec (Quebec city, Quebec, Canada), which has the capability to measure light reflection-related properties, as well as volume and moisture content data. Such wood chip inspection apparatus is basically described in U.S. Pat. No. 6,175,092 B1 issued on Jan. 16, 2001 to the present assignee, and will be now described in more detail in the context of the present invention.

Referring now to FIG. 2, the measurement station 12 shown is capable of generating color image pixel data through an optical inspection technique whereby polychromatic light is directed onto an inspected area of the wood chips, followed by sensing light reflected from the inspected area to generate the color image pixel data representing values of color components within one or more color spaces (RGB, HSL) for pixels forming an image of the inspected area. The measurement station 12 comprises an enclosure 14 through which extends a powered conveyor 15 coupled to a drive motor 18. The conveyor 15 is preferably of a trough type having belt 13 defining a pair of opposed lateral extensible guards 16, 16' of a known design, for keeping the wood chips to be inspected on the conveyor 15. In the embodiment shown on FIG. 2, only respective outlets 21 of screw devices 3 in communication with a main discharging screw device 17 are shown. It can be seen that the main discharging screw device 17 is adapted to receive through outlets 21 wood chips to be blended from corresponding wood chips sources. It is to be understood that the term "wood chips" is intended in the present specification to include other similar wooden materials for use as raw material for pulp production processes such as thermomechanical pulping (TMP), chemical-thermomecanical pulping (TCMP) or mechanical pulping (MP) processes, or for production processes of other wood-based products such as fibreboards (MDF, HDF), and that could be advantageously subjected to the methods in accordance with the present invention, such as flakes, shavings, slivers, splinters and shredded wood. The main screw device 17 has an elongated cylindrical sleeve 27 of a circular cross-section adapted to receive for rotation therein a feeding screw 28 of a known construction. The sleeve 27 has lateral input openings in communication with outlet 21 allowing wood chips to reach an input portion of the screw 28. The sleeve 27 further has an output 31 generally disposed over an input end of conveyor 15 to allow substantially uniform discharge of the wood chips 6 on the conveyor belt 13. The feeding screw 28 has a base disk 30 being coupled to the driven end of a driving shaft 32 extending from a drive motor 34 mounted on a support frame (not shown), which motor 34 imparts rotation to the screw 28 at a speed (RPM) in accordance with the value of the control signal coming from controller unit 33 through line 35', in order to modify the discharge rate of screw 28 to a desired target value. The driving control of screw devices 3 is performed in a similar way.

Figure 3:
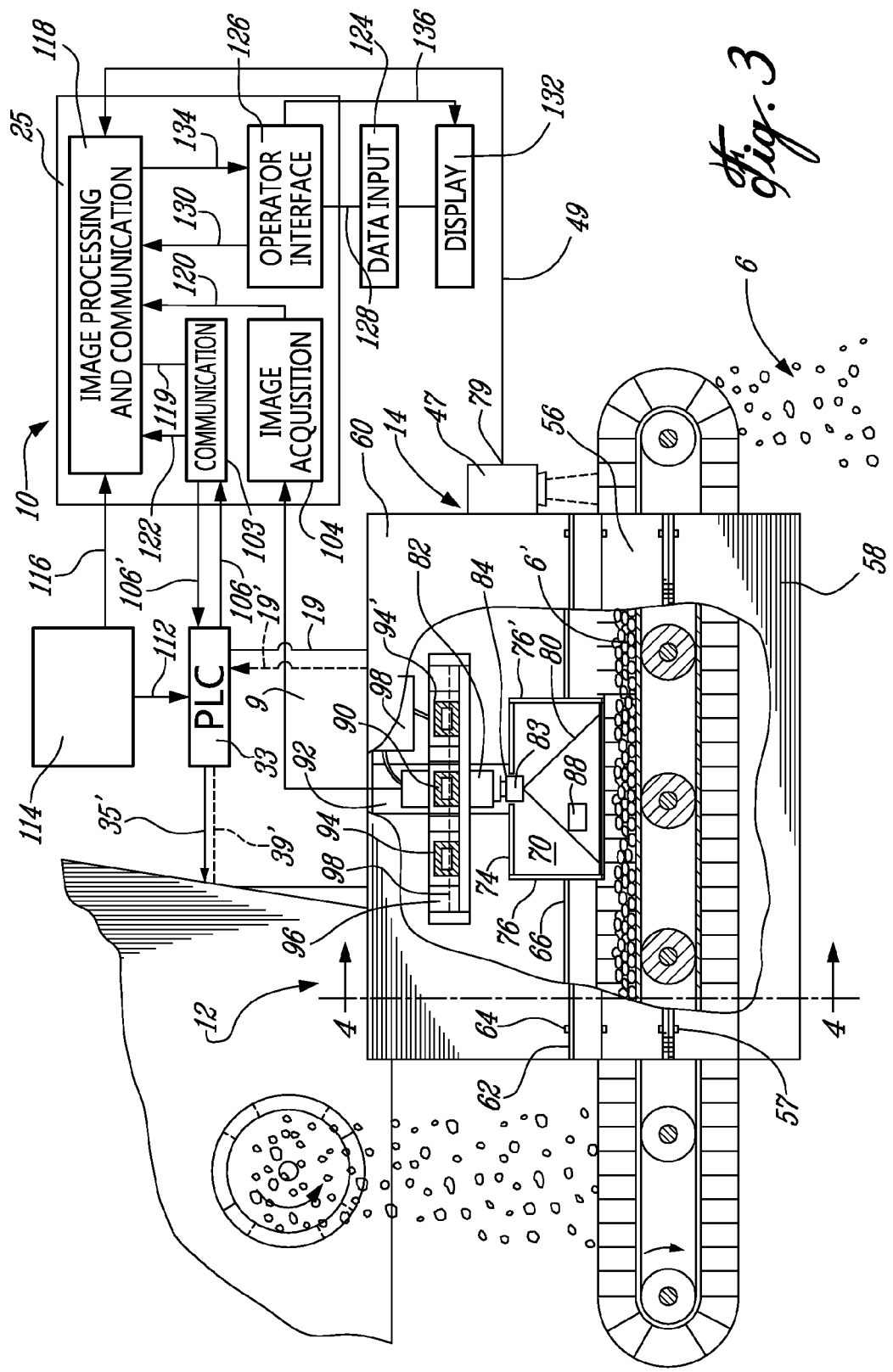
FIG. 3 is a partially cross-sectional side view along section line 3-3 of the measurement station shown on FIG. 2 and being connected to the data processor unit of FIG. 1 shown here in a detailed block diagram.
Figure 4:
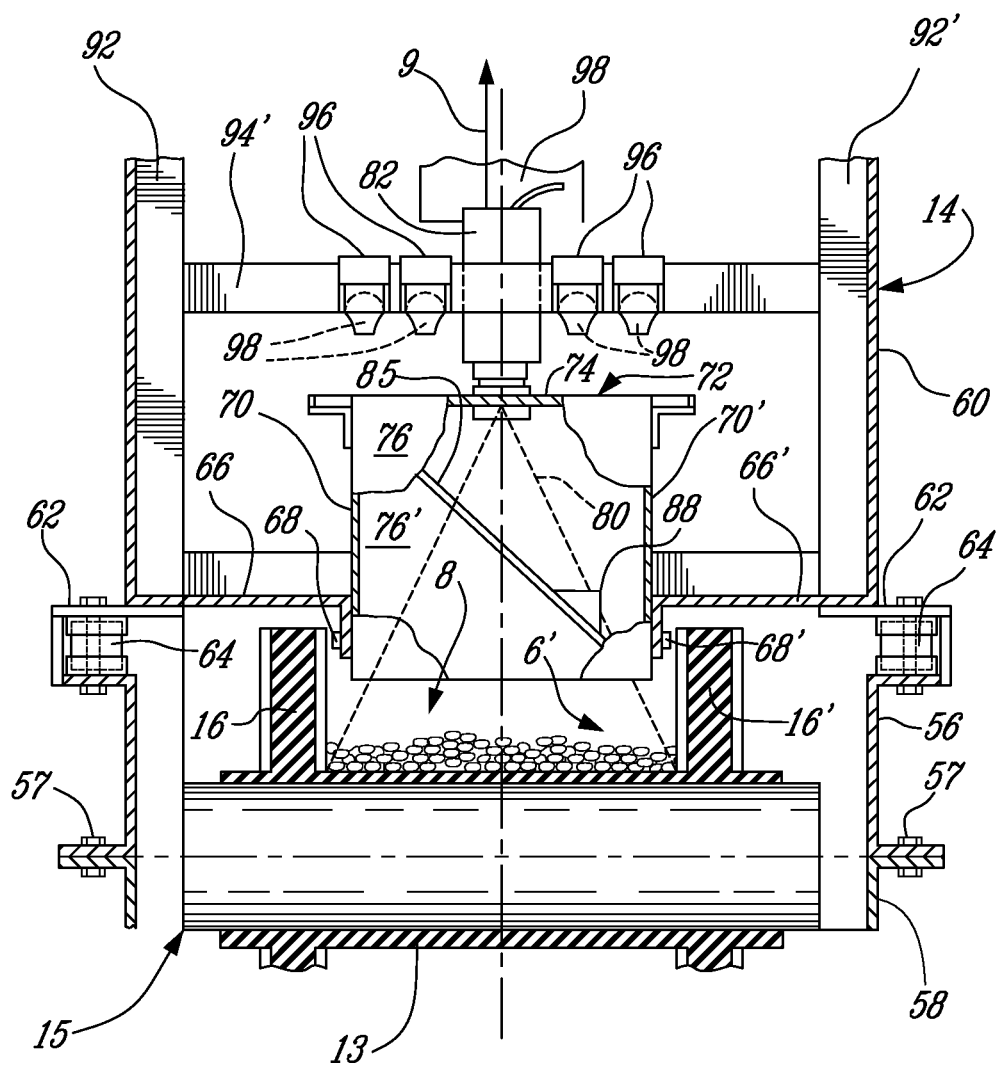
FIG. 4 is a partial cross-sectional end view along section line 4-4 of FIG. 3, showing the internal components of the measurement station.

Turning now to FIGS. 3 and 4, internal components of the measurement station 12 and particularly of the optical scanning unit 7 as shown on FIG. 1A will be now described. The enclosure 14 is formed of a lower part 56 for containing the conveyor 15 and being rigidly secured to a base 58 with bolt assemblies 57, and an upper part 60 for containing the optical components of the station 12 and being removably disposed on supporting flanges 62 rigidly secured to upper edge of the lower part 56 with bolted profile assemblies 64. At the folded ends of a pair of opposed inwardly extending flanged portions 66 and 66' of the upper part are secured through bolts 68 and 68' side walls 70 and 70' of a shield 72 further having top 74, front wall 76 and rear wall 76' to optically isolate the field of view 80 of a camera 82 for optically covering superficial wood chips 6' that are disposed within scanned area 8 as shown in FIGS. 1A and 4, these superficial wood chips 6' being considered as representative of the characteristics of substantially all wood chips 6. The camera 82 is located over the shield 72 and has an objective downwardly extending through an opening 84 provided on the shield top 74, as better shown on FIG. 3. Ideally, the distance separating camera objective 83 and superficial wood chips 6' should be kept substantially constant by controlling the input flow of matter, in order to prevent scale variations that could adversely affect the optical properties measurements. However, the selective discharge adjustment that can be applied to one or more of wood chips sources 1 to n according to the method of the invention does not generally allow a constant input flow through the measurement station 12. Therefore, the camera 82 is preferably provided with an auto-focus feature as well known in the art, and with a distance measuring feature to normalize the captured image data to compensate variation in the inspected area due to variation of the distance separating the camera reference plane and the superficial wood chips 6' within scanned area 8 as shown in FIGS. 1A and 4. The camera 82 is used to sense light reflected on superficial wood chips 6' to produce electrical signals representing reflection intensity values. A 2D CCD matrix, color RGB-HSL video camera such as Hitachi model no. HVC20 is used to generate the color pixel data as main optical properties considered by the method of the invention. While a 2D matrix camera is advantageously used to cover a 2D scanning area 8, it is to be understood that a suitable linear camera can alternatively be used by adapting the measurement station according to corresponding scanning parameters. Turning again to FIG. 4, diagonally disposed within shield 72 is a transparent glass sheet acting as a support for a calibrating reference support 88, whose function will be explained later in more detail. As shown on FIG. 3, the camera 82 is secured according to an appropriate vertical alignment on a central transverse member 90 supported at opposed end thereof to a pair of opposed vertical frame members 92 and 92' secured at lower ends thereof on flanged portions 66 and 66' as shown on FIG. 4. Also supported on the vertical frame members 92 and 92' are front and rear transverse members 94 and 94'. Transverse members 90, 94 and 94' are adapted to receive elongate electrical light units 96 used as illumination means, including standard fluorescent tubes 98 in the example shown, to direct light substantially evenly onto the inspected batch portion of superficial wood chips 6'. The camera 82 and light units 96 are powered via a dual output electrical power supply unit 100. Electrical image data are generated by the camera 82 through output line 9. The camera 82 is used to sense light reflected on superficial chips 6' to generate color image pixel data representing values of color components within RGB color space, for pixels forming an image of the inspected area, which color components are preferably transformed into color components within standard LHS color space, as will be explained later in more detail. When used in cold environment, the enclosure 14 is preferably provided with a heating unit (not shown) to maintain the inner temperature at a level ensuring normal operation of the camera 82. The apparatus 10 may be also provided with air condition sensors for measuring air temperature, velocity, relative humidity, which measurement may be used to stabilize operation of the measurement station.

Referring to FIG. 3, a moisture sensor 47 is shown which is preferably part of the measurement station 12. The sensor 47 is used measure variations in the chip surface moisture content. As will be explained later in detail, the chip moisture content that can be derived from such measurement is an important property that may be advantageously considered as an input variable of the model. The moisture sensor 47 is preferably a non-contact sensing device such as near-infrared sensor MM710 supplied by NDC Infrared Engineering, Irwindale Calif. The sensor 47 generates at an output 79 thereof electrical signals representing mean surface moisture values for the superficial wood chips 6'.

Control and processing elements of the measurement station 12 will be now described with reference to FIG. 3. The computer unit 25 used as a data processor, which has an image acquisition module 104 coupled to line 9 for receiving color image pixel signals from camera 82, which module 104 could be any image data acquisition electronic board having capability to receive and process standard image signals such as model Meteor-2™ from Matrox Electronic Systems Ltd (Canada) or an other equivalent image data acquisition board currently available in the marketplace. The computer 25 is provided with an external communication unit 103 being coupled for bi-directional communication through lines 106 and 106' to controller unit 33, which is a conventional programmable logic controller (PLC) programmed for controlling operation of each discharge screw device 3 and main screw device 17 through control lines 35, 35' and feedback line 39'39', as well as conveyor drive 18 through line 19 and feedback line 19' coupled to the drive mechanism of the conveyer 15 to provide a signal indicating of the effective conveyer belt speed. The PLC 33 may receive from line 112 wood chips source data entered via an input device 114 by an operator in charge of raw wood chips management operations, such as wood chips species information. The input device 114 is connected through a further line 116 to an image processing and communication software module 118 outputting control data for PLC through line 119 while receiving acquired image data and PLC data through lines 120 and 122, respectively. The image processing and communication module 118 receives input data from a computer data input device 124, such as a computer keyboard, through an operator interface software module 126 and lines 128 and 130, while generating image output data toward a display device 132 through operator interface module 126 and lines 134 and 136. Module 118 also receives the moisture indicating electrical signals through a line 49.

Figure 5:
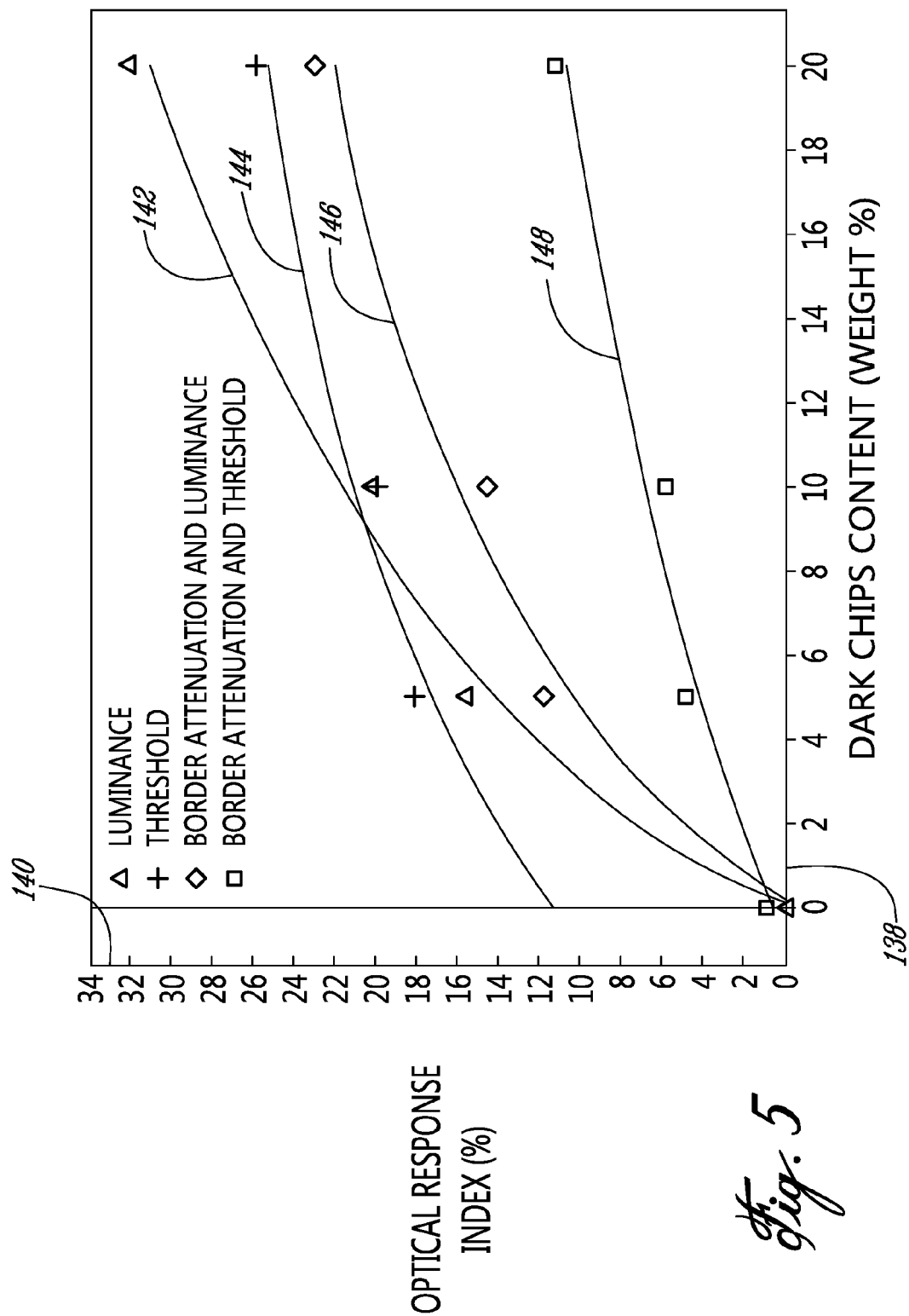
FIG. 5 is a graph showing a set of curves representing general relations between measured optical characteristics and dark wood chips content associated with several samples.

Turning now to FIG. 5 general relations between measured optical characteristics and dark wood chips content associated with several samples are illustrated by the curves traced on the graph shown, whose first axis 138 represents dark chips content by weight percentage characterizing the sample, and whose second axis 140 represents corresponding optical response index measured. In the example shown, four curves 142, 144, 146, and 148 have been fitted on the basis of average optical response measurements for four (4) groups of wood chips samples prepared to respectively present four (4) distinct dark chips contents by weight percentage, namely 0% (reference group), 5%, 10% and 20%. Measurements were made using a RGB color camera coupled to an image acquisition module connected with a computer, as described before. To obtain curves 142 and 146, luminance signal values derived from the RGB signals corresponding to all considered pixels were used to derive an optical response index which is indicative of the relative optical reflection characteristic of each sample. As to curve 142, mean optical response index was obtained according to the following ratio:

$$I = \frac{L_R}{L_S} - 1 \qquad (8)$$

Wherein I is the optical response index, $L_R$ is a mean luminance value associated with the reference samples and $L_S$ is a mean luminance value based on all considered pixels associated with a given sample. Curve 146 was obtained through computer image processing to attenuate chip border shaded area which may not be representative of actual optical characteristics of the whole chip surface. To obtain curves 144 and 148, reflection intensity of red component of RGB signal was compared to a predetermined threshold to derive a chip darkness index according the following relation:

$$D = \frac{P_D}{P_T} \qquad (9)$$

Wherein D is the chip darkness index, $P_D$ is the number of pixels whose associated red component intensity is found to be lower than the predetermined threshold ratio (therefore indicating a dark pixel) and $P_T$ is the total number of pixels considered. As for curve 146, curve 148 was obtained through computer image processing to attenuate chip border shaded areas. It can be seen from all curves 142, 144, 146, and 148 that the chip darkness index grows as dark chip content increases. Although curve 148 shows the best linear relationship, experience has shown that all of the above described calculation methods for the optical response index can be applied, provided reference reflection intensity data are properly determined, as will be explained later in more detail.

Returning now to FIGS. 2, 3 and 5, a preferred operation mode of the chip optical properties inspecting function of the measurement station 12 will be now explained. Referring to FIG. 3, before starting operation, the station 12 must be initialized through the operator interface module 126 by firstly setting system configuration. Camera related parameters can be then set through the image processing and communication module 118, according to the camera specifications. The initialization is completed by camera and image processing calibration through the operator interface module 126.

System configuration provides initialization of parameters such as data storage allocation, image data rates, communication between computer unit 25 and PLC 33, data file management, and wood species information. As to data storage allocation, images and related data can be selectively stored on a local memory support or any shared memory device available on a network to which the computer unit 25 is connected. Directory structure is provided for software modules and system status message file. Image rate data configuration allows to select total number of acquired images for each batch, number of images to be stored amongst the acquired images and acquisition rate, i.e. period of time between acquisition of two successive images which is typically of about 5 sec. for a conveying velocity of about 10 feet/min. Therefore, to limit computer memory requirements, while a high number of images can be acquired for statistical purposes, only a part of these images need to be stored, and most of images are deleted after a predetermined period of time. The PLC configuration relates to parameters governing communication between computer unit 25 and PLC 33, such as master-slave protocol setting (ex. DDE), memory addresses associated with « heart beat» for indication of system interruption, « heart beat» rate and wood chips presence monitoring rate. Data file management configuration relates to parameters regarding wood chips Input data, statistical data for inspected wood chips, data keeping period before deletion and data keeping checking rate. Statistical data file can typically contain information relating to source or batch number, supplier contract number, wood species identification (pure/ mixture), mean intensity values for RGB signals, mean luminance L, mean H (hue) and mean S (saturation), darkness index D and date of acquisition. Data being systematically updated on a cumulative basis, the statistical data file can be either deleted or recorded as desired by the operator to allow acquisition of new data. Once the camera 82 is being configured as specified, calibration of the camera and the image processing module can be carried out by the operator through the operator interface, to ensure substantially stable light reflection intensities measurements as a function of time even with undesired lightning variation due to temperature variation and/or light source aging, and to account for spatial irregularities inherent to COD's forming the camera sensors. Calibration procedure first consists of acquiring « dark» image signals while obstructing with a cap the objective of the camera 82 for the purpose of providing offset calibration (L=0), and acquiring « lighting» image signals with a gray target presenting uniform reflection characteristics being disposed within the inspecting area on the conveyer belt 13 for the purpose of providing spatial calibration. Calibration procedure then follows by acquiring image signals with an absolute reference color target, such as a color chart supplied by Macbeth Inc., to permanently obtain a same measured intensity for substantially identically colored wood chips, while providing appropriate RGB balance for reliable color reproduction. Initial calibration ends with acquiring image signals with a relative reference color target permanently disposed on the calibrating reference support 88, to provide an initial calibration setting which account for current optical condition under which the camera 82 is required to operate. Such initial calibration setting will be used to perform calibration update during operation, as will be later explained in more detail.

Initialization procedure being completed, the measurement station 12 is ready to operate, the computer unit 25 being in permanent communication with the PLC 33 to monitor the operation of screw drive 34 indicating discharge of wood chips blend from the sources. Whenever a new batch is detected, the following sequence of steps are performed: 1) end of PLC monitoring; 2) source or batch data file reading (species of wood chips, source or batch identification number); 3) image acquisition and processing for wood species proportion estimation; and 4) data and image recording after processing. Image acquisition consists in sensing light reflected on the superficial wood chips 6' included in a currently inspected batch portion to generate color image pixel data representing values of color components within RGB color space for pixels forming an image of the inspected area 8 defined by camera field of view 80. Although a single batch portion of superficial chips covered by camera field of view 80 may be considered to be representative of optical characteristics of a substantially homogeneous batch, wood chips batches being known to be generally heterogeneous, it is preferable to consider a plurality of batch portions by acquiring a plurality of corresponding image frames of electrical pixel signals. In that case, image acquisition step is repeatedly performed as the superficial wood chips of batch portions are successively transported through the inspection area defined by the camera field of view 80. Calibration updating of the acquired pixel signals is performed considering pixel signals corresponding to the relative reference target as compared with the initial calibration setting, to account for any change affecting current optical condition. Superficial wood chips 6' are also scanned by infrared beam generated by the sensor 47, which analyzes reflected radiation to generate the chip surface moisture indication signals. It is to be understood that while the moisture sensor 47 is disposed at the output of the measurement station 12 in the illustrated embodiment, other locations downstream or upstream to the measurement station 12 may be suitable.

As to image processing, the image processing and communication unit 118 is used to derive the luminance-related data, preferably by averaging luminance-related image pixel data as basically expressed as a standard function of RGB color components as follows:

$$L=0.2125R+0.7154G+0.0721B \tag{10}$$

Values of H (hue) and S (saturation) are derived from RGB data according to the same well known standard, hue being a pure color measure, and saturation indicating how much the color deviates from its pure form, whereby an unsaturated color is a shade of gray. As mentioned before, the unit 118 derives global reflection intensity data for the inspected batch portions designated before as optical response index with reference to FIG. 5, from the acquired image data. For example, experience has shown that spruce and balsam fir are brighter than jack pine and hardwood, and chip ageing and bark content decrease chip brightness. Calibration updating of the acquired pixel signals is performed considering pixels signals corresponding to the relative reference target as compared with the initial calibration setting, to account for any change affecting current optical condition. Then, image noise due to chip border shaded areas, snow and/or ice and visible belt areas are preferably filtered out of the image signals using known image processing techniques. From the signals generated by moisture sensor 47, the image processing and communication unit 118 applies compensation to the acquired pixel signals using the corresponding moisture indicating electrical signals.

Global reflection intensity data may then be derived by averaging reflection intensity values represented by either all or representative ones of the acquired pixel signals for the batch portions considered, to obtain mean reflection intensity data. Alternately, the global reflection intensity data may be derived by computing a ratio between the number of pixel signals representing reflection intensity values above a predetermined threshold value and the total number of pixel signals considered. Any other appropriate derivation method obvious to a person skilled in the art could be used to obtain the global reflection intensity data from the acquired signals. Optionally, the global reflection intensity data may include standard deviation data, obtained through well known statistical methods, variation of which may be monitored to detect any abnormal heterogeneity associated with an inspected batch.

In operation, the computer unit 25 continuously sends a normal status signal in the form of a « heart beat » to the PLC through line 106'. The computer unit 25 also permanently monitors system operation in order to detect any software and/or hardware based error that could arise to command inspection interruption accordingly. The image processing and communication module 118 performs system status monitoring functions such as automatic interruption conditions, communication with PLC, batch image data file management and monitoring status. These functions result in messages generation addressed to the operator through display 132 whenever appropriate action of the operator is required. For automatic interruption conditions, such a message may indicate that video (imaging) memory initialization failed, an illumination problem arose or a problem occurred with the camera 82 or the acquisition card. For PLC communication, the message may indicate a failure to establish communication with PLC 33, a faulty communication interruption, communication of a « heart beat » the PLC 33, starting or interruption of the « heart beat ». As to batch data files management, the message may set forth that acquisition initialization failed, memory storing of image or data failed, a file transfer error occurred, monitoring of recording is being started or ended. Finally, general operation status information is given to the operator through messages indicating that the apparatus is ready to operate, acquisition has started, acquisition is in progress and image acquisition is completed. As mentioned above, the measurement station is able to perform on-line measurement of chip physical properties, such as moisture content, darkness indication, H (Hue), S (Saturation) and L (Luminance), basic and bulk densities, dry and wet weight.

Figure 7:
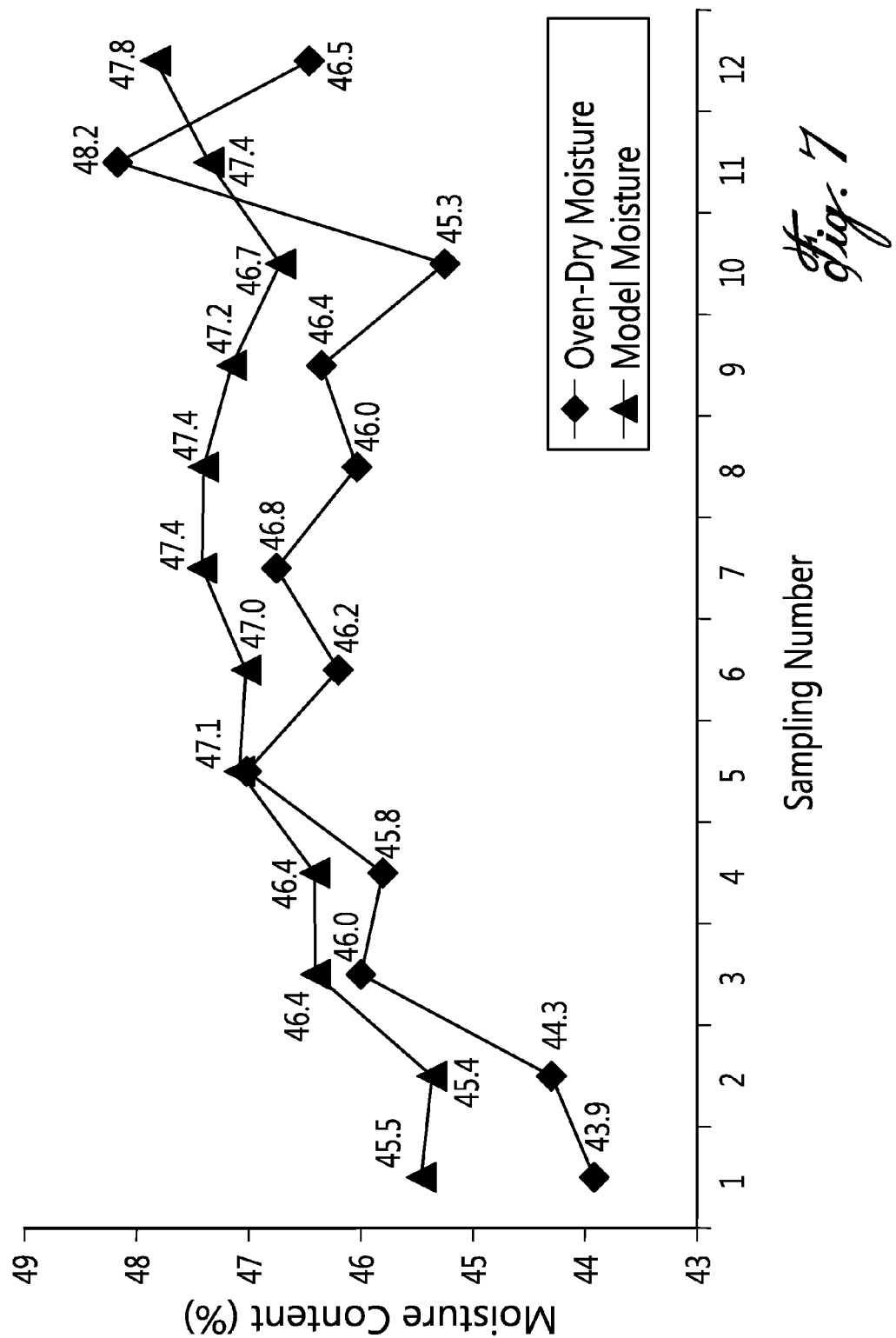
FIG. 7 is a graph presenting the results of a validation of on-line moisture content measurement.

Referring now to FIG. 7, the results of a validation of on-line moisture content measurement is presented, in which the wood species is a mixture of Fir, Spruce, Hemlock, Pine and Hardwood, and their respective proportions are unknown. The test period extended over six month from spring to fall, and measurement accuracy was estimated within about ±1%. Furthermore, tests were performed in a TMP mill to study the impacts of the stabilization of the dry-based density on refining energy consumption.

In operation, based on the principle of the present invention, on-line measurements can be combined with control of the speed of the chip feeding screw associated with each pile to produce substantially stable values for chip dry-based density, before chips enter the processing stage upstream the refiner process. The invention can also help operators to better control plate gap, dilution water rate in view of production rate, specific energy and consistency control, and also can serve to warn operators whenever unacceptable chips are likely to enter the process and negatively impact pulp quality. As mentioned above, the measurement station provides on-line information on chip brightness, bark content, chip dynamic weight, moisture, chip wet and dry mass flow rate, basic and bulk density, volume flow rate and proportions of wood chips from the different piles. When installed in the chip feeding process, the measurement station generates on-line chip characteristics information that can be used to control the mixture of chips from the different piles in order to stabilize the dry-based density of wood chips entering the discs of the refiners.

Figure 8:
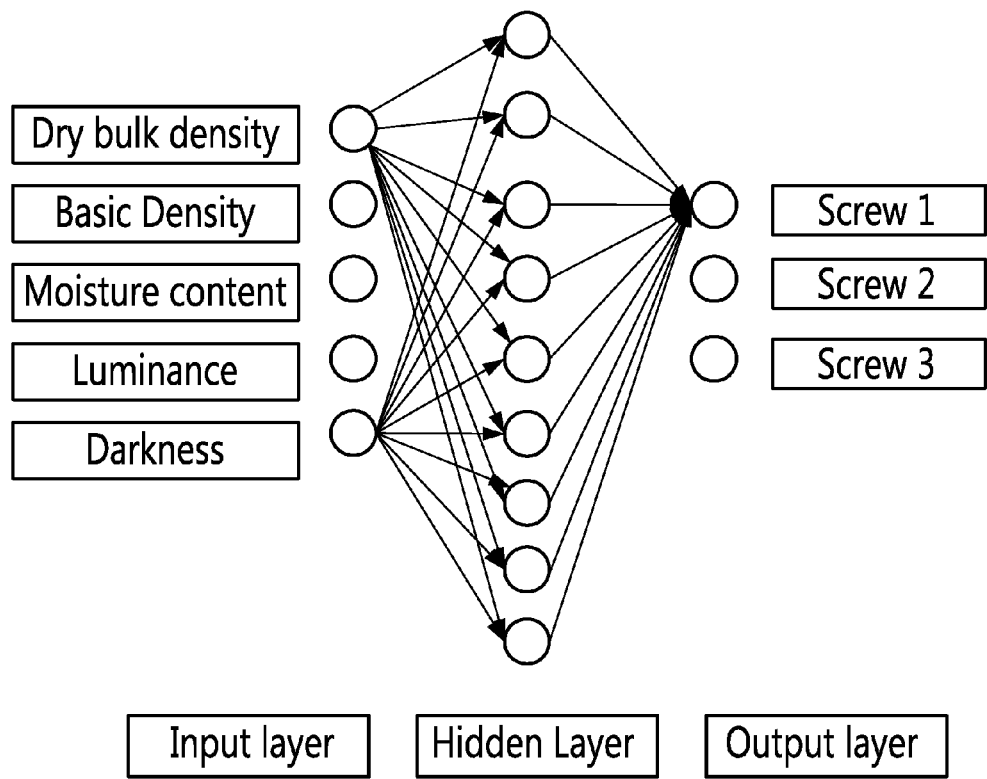
FIG. 8 is a schematic representation of an exemplary neural network structure relating the screw speeds of the chip discharging sources with the on-line measurements.

The details regarding the appropriate reference model to be used will now be presented. The ideal approach to stabilize the input density of the chips would be to make a physical model which relates the measurements of the system and the density of the chips as extracted by the screw devices 3. Unfortunately, this approach is not feasible since the physical process which relates the incoming density of the chips with the screw speeds is unknown. A solution consists of building an empirical, reference model established from practical examples relating the screw speeds with the measurements of the system. Historical data are needed from which one can relate the screw speeds to the input density. A neural network is an appropriate tool to build this model. Neural networks are interesting because of their ability to generalize their output when they are fed with unknown inputs, provided that they remain in a reasonable range. They can also model non-linear processes. It is to be understood that other techniques such as PLS or Fuzzy logic may also be used to implement the reference model. There is a need to associate the density (and other variables) measured by the system and the speed of the screw devices 3. The controller 33 must be able to adjust the speeds depending on the value of the density. The neural network will need the speed of each screw and the basic density of the chips. Further variables are also used in order to facilitate the convergence of the learning process. This way, screw speeds will be mainly determined by the input density but also by other variables, namely light reflection-related property (such as luminance) and moisture content of the chips. A neural network implementation was done with Matlab™ version 7.4 (R2007a) and neural network toolbox 5.0.2 (R2007a). Any other appropriate programming tool for the creation, training and testing of neural networks could also be used. A feed-forward neural network trained with the Levenberg-Marquardt algorithm was used. This algorithm is a combination of steepest descent algorithm and Newton's method to minimise the output error. It is generally a very fast algorithm. An exemplary neural network structure is shown in FIG. 8, involving dry-based density properties (dry bulk density, basic density), moisture content and light reflection-related properties (luminance, darkness index). All neurons from one layer are connected to all neurons on the following layer. All connections are not represented for ease of illustration. To train the network, a plurality of chip blends were obtained with different screw speeds. The different measurements provided by the system were then associated with these specific speeds. Table 2 indicates typical proportions of the speeds of the three silos. The numbers represent the percentage of input from each screw, which totalize 100%.

TABLE 2

| Blend no. | Speed proportion |
|---|---|
| 1 | 70 - 15 - 15 |
| 2 | 75 - 15 - 10 |
| 3 | 75 - 10 - 15 |
| 4 | 80 - 10 - 10 |
| 5 | 75 - 19 - 6 |
| 6 | 80 - 20 - 0 |
| 7 | 88 - 12 - 0 |
| 8 | 93 - 0 - 7 |
| 9 | 88 - 0 - 12 |
| 10 | 70 - 20 - 10 |
| 11 | 70 - 15 - 15 |
| 12 | 75 - 20 - 5 |
| 13 | 75 - 10 - 15 |
| 14 | 89 - 11 - 0 |

Figure 9:
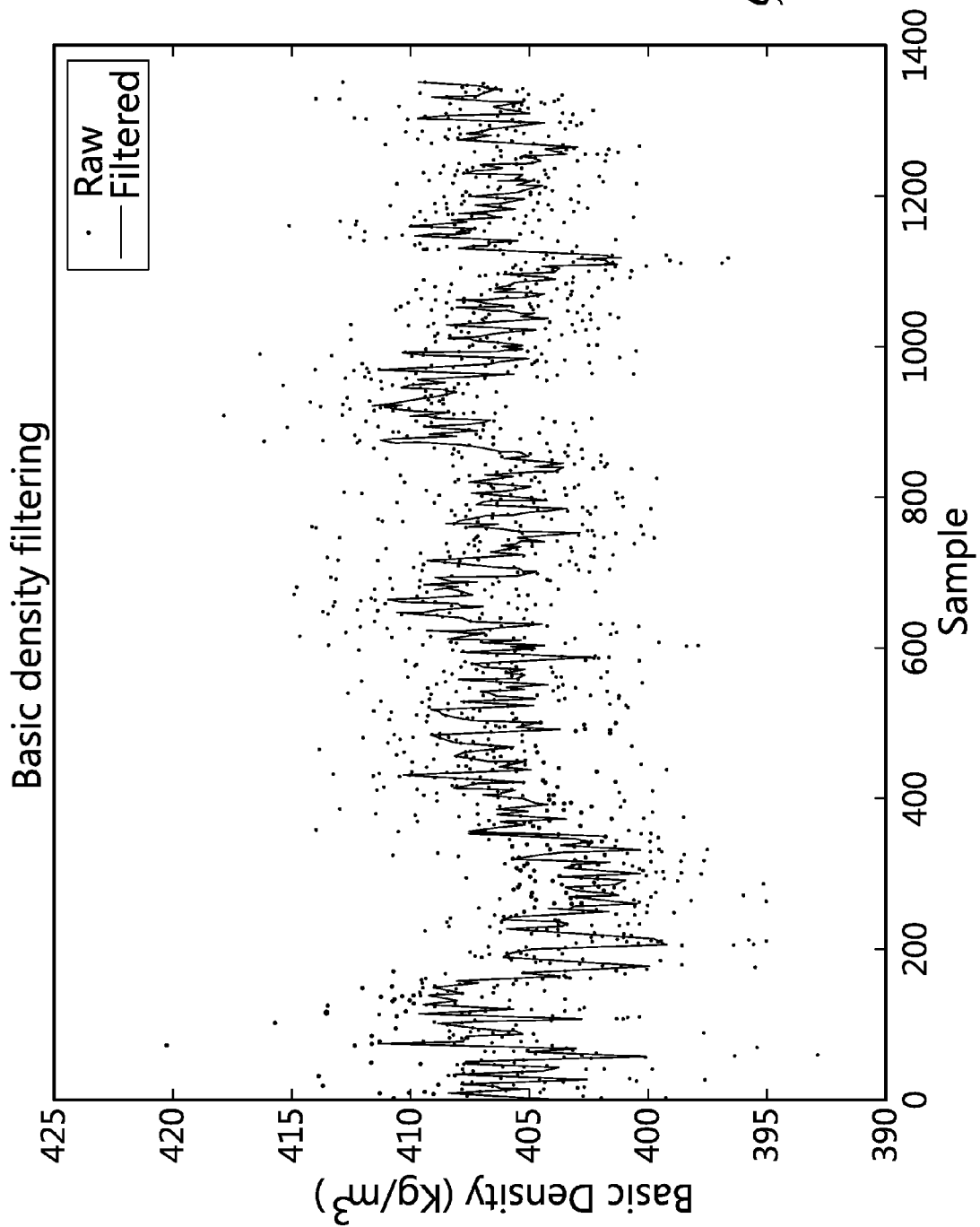
FIG. 9 is a graph showing the effect of filtering of raw basic density data for the purpose of neural network training.

These examples are representative of the regular blends used by the mill at different moments. The blends with a screw contribution of 0% (nos. 6-9 and 14) are of less interest because a silo should not be stagnant for a long period of time. All the data was stored in the mill's database. An average of 20 seconds was used to generate each data point of the training data. To generate the training set, the first step is to determine the delay between speed readings and density measurements. There is a known distance between the screws and the measurement station, so the delay between mixing and readings must be evaluated. By doing a statistical analysis between the measurements and the screw speeds it is possible to determine the delay. The method consists of evaluating the correlation between the input vectors for different values of the possible delay. The maximum correlation should be near the real delay. This method is not perfect, but gives a good first estimate. In the performed experiments, the delay was estimated to be around five minutes. Since the data is represented as a vector wherein each position represents a 20 seconds average, the elements of the measurement vectors were shifted by 15 samples with respect to those of the screws. Once the data was acquired, it was filtered to eliminate invalid data and to reduce the amount of noise. The data coming from the screws being preset, no filtering was needed. Data processing started by eliminating negative values, NaNs (Not a Number), and outliers present in the data. The effect of filtering on the raw density data (basic density) can be seen on FIG. 9.

The following values obtained from the measurement station were used to determine the inputs to the network: basic density and/or dry bulk density, moisture content and light reflection-related property (luminance, darkness index). The dry bulk density was computed from the bulk density and the moisture content according to the following relation:

$$\rho_{dry\ bulk} = \rho_{bulk} \frac{100 - \text{moisture content}}{100} \quad (11)$$

All the measurement data was filtered with a mobile average on a window of 5 elements. This helped to eliminate spikes and strong variations of the input density which did not represent a realistic estimate, average and long term behaviours being of interest. A matrix was generated each column corresponding to one variable. In order, the variables are basic density, dry bulk density, moisture content, luminance and darkness. An output matrix was also created, each column corresponding to the relative speed of each screw. From this data set, the training process started. For this particular run a network with 5 input neurons, 9 hidden neurons and 3 output neurons was created. There were a total of 2239 samples for each variable in our set. Since each point represented 20 seconds of data, over 12 hours were distributed over a 2 month period. The learning process involved separating our data into three sets. The training set was composed of 60% of the data, the validation set composed of 20%, and the testing set composed the remaining 20%. The network was trained with the training set. The validation set was used to control the learning process so as to not over-learn. If the learning procedure is not stopped early enough, then the associations learned by the network will be rigid, will not tolerate any deviation from the learning data, and the network will then be poor at generalization. This must be avoided considering the fluctuation of the input data. The testing set gave the performance of the network in the presence of data not used for training. All members of the three sets were determined randomly. The network was then trained with the Levenberg-Marquardt algorithm. Normally the regression R values of the three sets should be near 1. The results obtained for the training run are shown in Table 3.

TABLE 3

| Set | MSE | R |
|---|---|---|
| Training | 0.00964 | 0.9974 |
| Validation | 0.0143 | 0.9962 |
| Testing | 0.0238 | 0.9819 |

The results indicate that the network was able to learn the associations and thus functional. It is important to note that the neural network training is one of the most important factors for determining the success of the implementation. If the training set is inappropriate, the performance of the model itself will be unsuitable. One must ensure that as much of the input and output variations are covered. The training set may also take into account the seasonal variations by accumulating data from different seasons and conditions.

At that point, the model is capable of tying the measurement values to the screw speeds and thus the proportion of each silo into the mix. The ultimate function of the model is to compare the estimated dry-based density with a predetermined target density to produce error data, and to selectively modifying discharge rate set points of one or more of the wood chip sources (silos) to minimize the error data within fluctuation limits around the target. In practice, the target density is conveniently chosen so that it is not too far from the density readings of the measurement system. The fluctuation limits around the target density (over and under) are then established. If the error data is within these limits then no command to change the screw speed is generated by the model.

The Matlab™ compiler was used to add the neural model to the measurement system implementation, whereby the Matlab™ code receives the measurement values and feeds them through the model, to selectively modify the discharge rate set points of the corresponding screws. The model may be programmed to never take an action if one of the inputs is found invalid for whatever reason. Whenever the program detects an invalid input or an abnormal condition, the program maintains the last valid discharge rate set points. Conveniently, due to the delay between chip mixing and measurements, the program is set to wait at least 10 minutes before making any decision to change the discharge rate set points. Since density change is a relatively slow process, it might be necessary in some cases to increase the delay to 15 or even 20 minutes.

No matter what the delay is between two measurements, in the present example, the model always receives 5 measurements (samples) representing an average computed within that time interval divided by the same number of samples (15). For example, if the delay is set to 10 minutes, then each point represents an average of 40 seconds. Once the data is received from the measurement station, the program verifies the validity of the samples to prevent changes based on faulty data. This validation step will reject a sample if there is any measurement anomaly or in case of screw devices malfunction, to avoid the situation where one silo is no longer used and starts to accumulate chips. The validation step can include a verification if the density measurements fall within the range of the training data. Once the data had been validated, the measured density at the input of the model was replaced by the target density for all 15 measurement elements. The corresponding screw speeds for all of them were predicted and the average of the 15 predictions was taken as the new screw speeds. Considering that screws have preset operation limits, If a set point modification brings two or more of them beyond their operation limits, the program may reset the set points to more reasonable values and restart the process therewith. In that manner, the screws do not get stuck in a configuration that would prevent the target density to be approached within the fluctuation limits.

The target dry-based density is one of the inputs of the reference model, which connects the values of the measurement system to corresponding discharging screw speeds. The model determines the discharge rate set points to be used according to the difference (error) between the estimated dry-based density and the predetermined target density. The model establishes fluctuation limits based on a tolerable error (±threshold) on the estimated dry-based density around the target to avoid unnecessary screw speed change. No action is taken by the model if the error on the dry-based density estimated by the measurement system is within the fluctuation limits.

Figure 10:
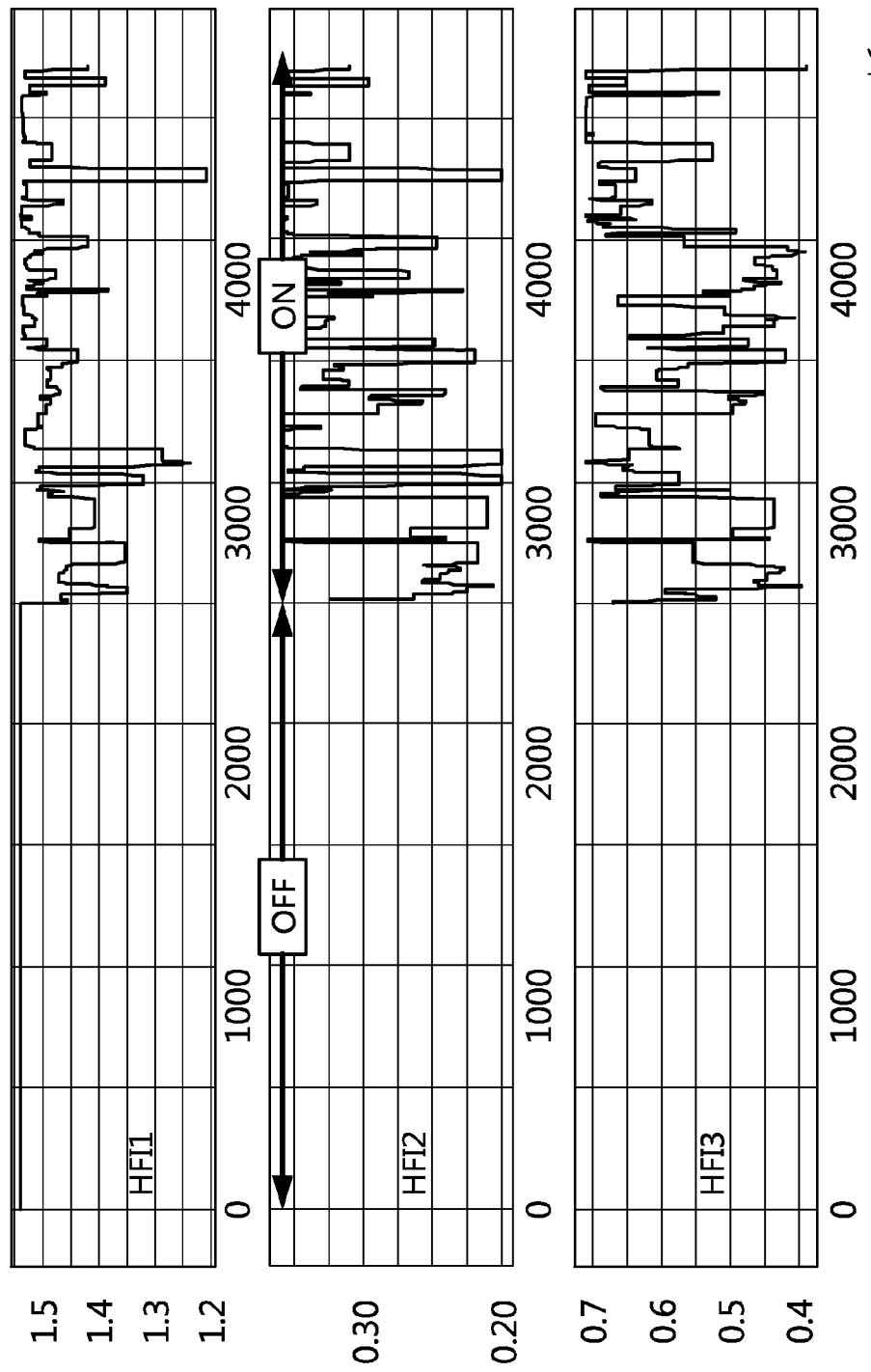
FIG. 10 are graphs comparing the discharge rate set points of screw devices without and with dry-based density stabilization.

Validation tests of the model were performed at a mill to measure the reduction of variability of dry-based density, i.e. stabilization around the target, and to evaluate the energy savings associated with the stabilization. For that purpose, stabilization "ON" periods were compared with stabilization " OFF " periods as shown in FIG. 10, wherein it can be observed that when the screws were not under the control of the model, the chip discharge rate set points of the screws were constants. Subsequently, when the screws were under control of the model, it can be seen that the discharge rate set points were selectively modified accordingly. The aim of these modifications was to stabilize the dry-based density mixture of chips around the predetermined target.

Figure 11:
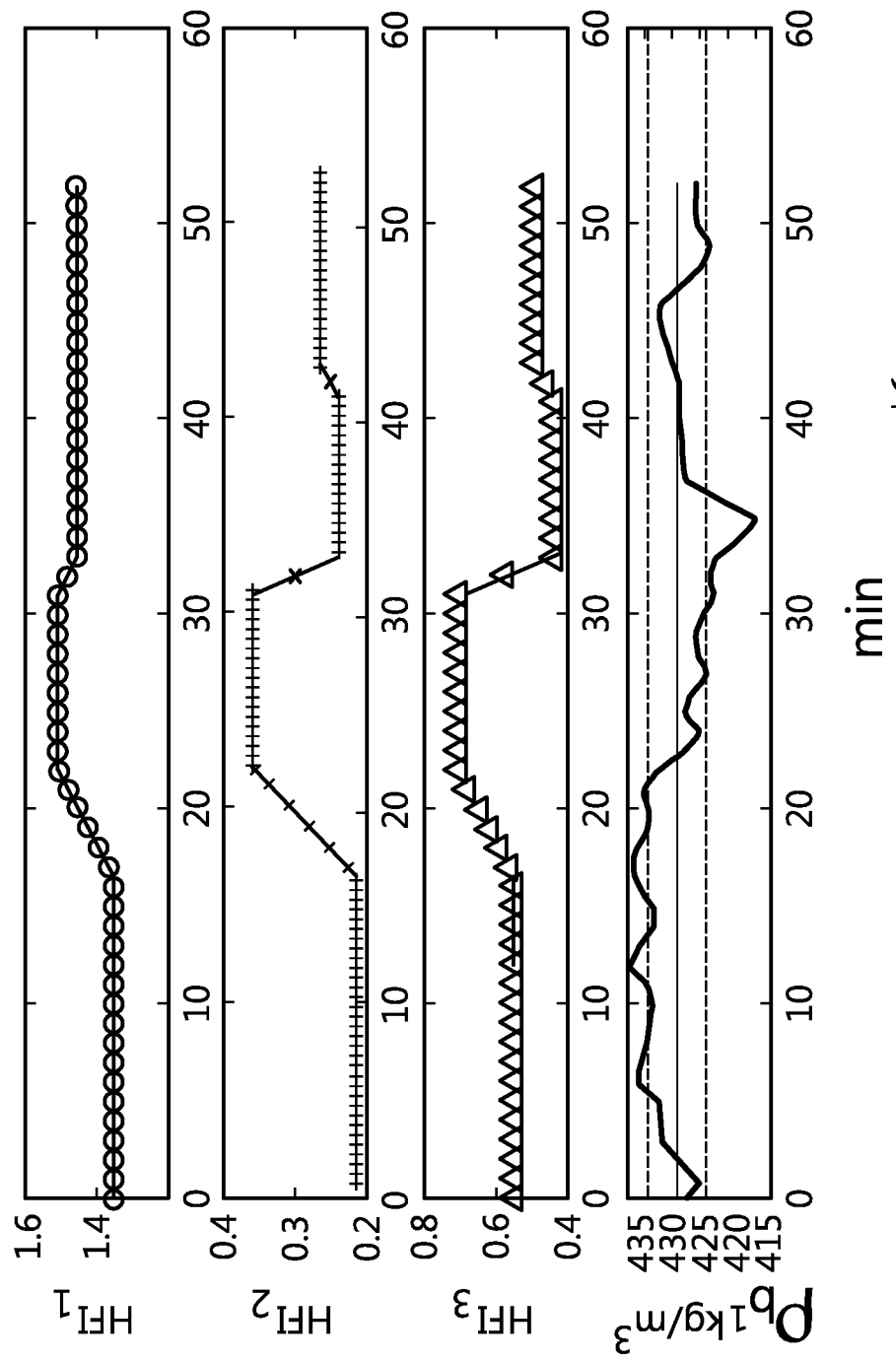
FIG. 11 shows a graph of dry-based density variations over time compared with graphs of discharge rate set points of screw devices under control to stabilize dry-based density.

The reaction to stabilization of dry-based density of chips is illustrated in FIG. 11. When the density of chips tends to fall beyond the upper or lower limits, the set points of chip discharge rate are modified to bring the density back toward the target. The screw devices are controlled by changing their discharge rate, to control the proportion of chips from each source in the mixture. For the example shown, when the density tends to exceed the upper limit of dry-based density, the control is performed to reduce the percentage of spruce (pile 1) and to increase the percentages of pine and hardwood (piles 2 and 3) in the mixture. When the density tends to drop under the lower limit of dry-based density, the control is performed to increase the percentage of spruce (pile 1) and reduce the percentages of pine and hardwood (piles 2 and 3).

Figure 12:
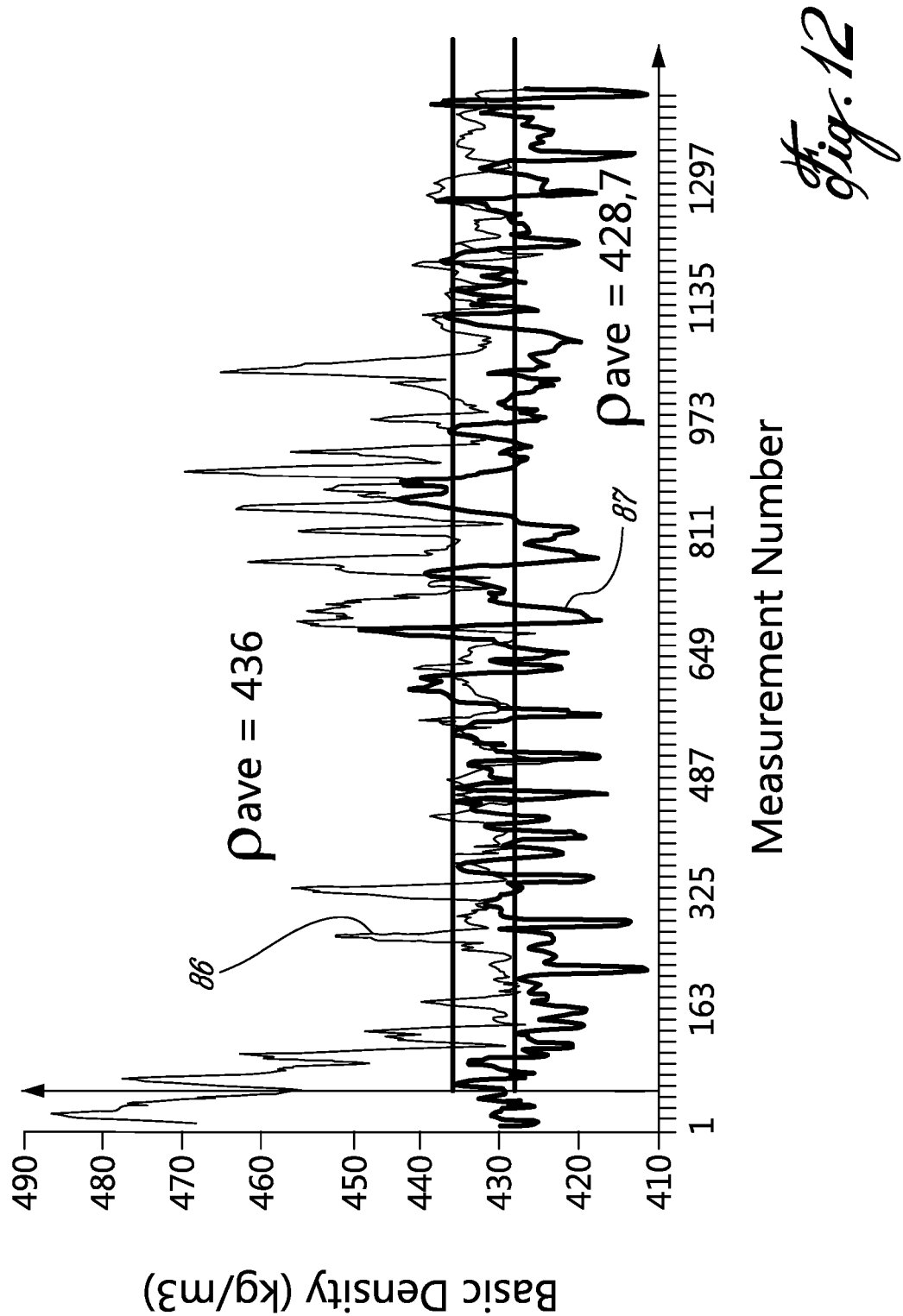
FIG. 12 is a graph comparing dry-density variation curves obtained without and with dry-based density stabilization.

Referring now to FIG. 12 it can be seen that variability of the basic density during the stabilization "ON" period as represented by curve 87 was lower than during the stabilization "OFF" period represented by curve 86. For the "OFF" period, the average density was 436.8 (kg/m3) and standard deviation was 11.3 , while for the "ON" period, the average density was 428.6 (kg/m3) and standard deviation was 6.9. The standard deviation (variability) decreased from 11.3 to 6.9, which represents a significant, 30% reduction of variability of chip mixture density.

Figure 13:
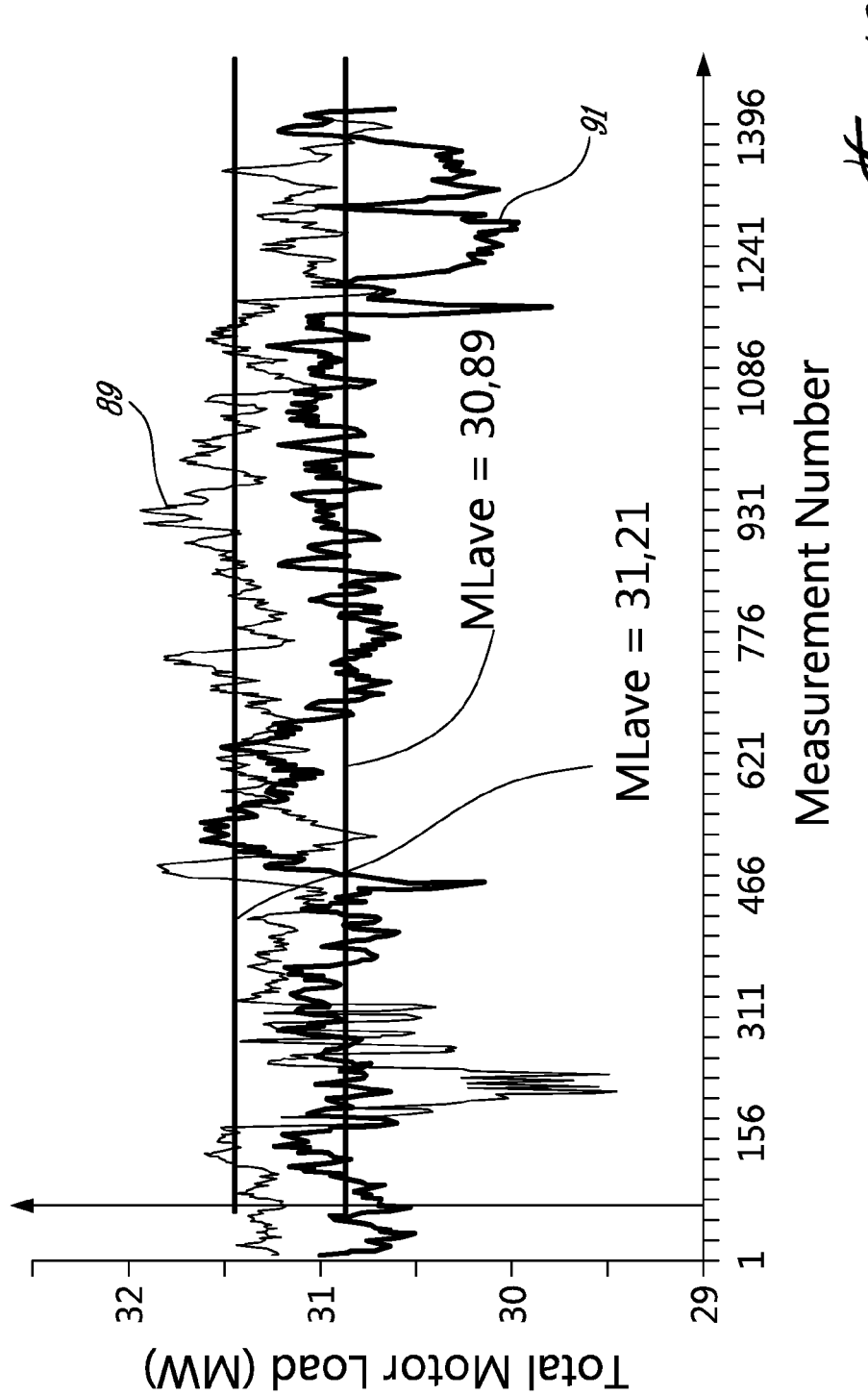
FIG. 13 is a graph comparing total refining motor load curves obtained without and with dry-based density stabilization.

The impact of dry-based density stabilization on the operation of refining will now be discussed in view of FIG. 13. The stabilization of dry-based density resulted in a stabilization of the refining operation particularly in term of total motor load. For the stabilization "OFF" period as represented by curve 89, the average motor load was 31.21 (MW.h) with a standard deviation of 0.50. For the stabilization "ON" period represented by curve 91, average motor load was 30.89 (MW.h) with a standard deviation of 0.40. With the stabilization of basic density, the motor load decreased of 0.31 MW.h (from 31.21 to 30.89 MW.h) and standard deviation (variability) decreased from 0.50 to 0.40, which represents a 10% of reduction. For the dry-based density stabilization period, the motor load for secondary refining was reduced significantly and the control of the refiner feed screw was very active.

Figure 14:
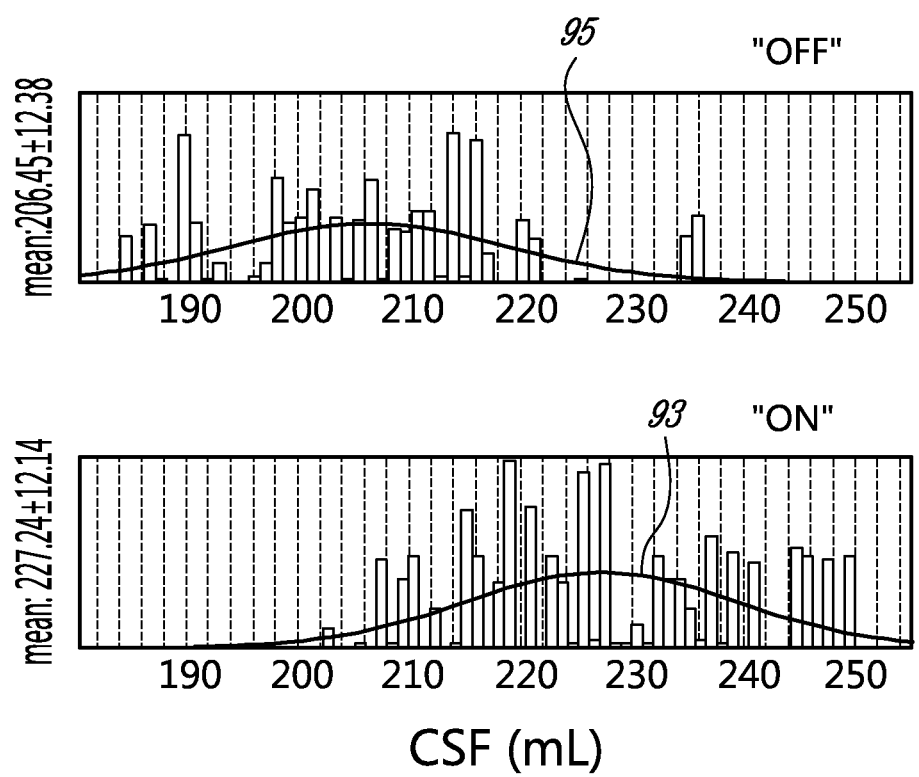
FIG. 14 shows graphs comparing CSF of pulp obtained without and with dry-based density stabilization.

The effect of dry-based density stabilization on pulp quality stabilization will now be discussed with reference to FIG. 14, which shows a comparison of CSF (Canadian Standard Freeness) for the "OFF" and "ON" stabilization periods. For the "ON" period represented by curve 93, the standard deviation was slightly lower (12.14 versus 12.38) than for the "OFF" period represented by curve 95. Although the average CSF for "ON" period was higher than for "OFF" period (227.24 versus 206.45 ml), no poor paper quality has been reported by the mill during testing. In that mill, the only available measurement of pulp quality was CSF, and the measurement of CSF was made periodically with intervals of 40-50 minutes, which did not permit to see the variability between measurements. The CSF cannot be directly used to estimate the impact of the stabilization of the chip dry-based density on the pulp quality. At that mill, variation control of CSF was primarily performed through reject flow rate control. If the CSF was found still unstable after controlling the reject flow rate, further control through plate hydraulic pressure was then performed. In the stabilization "ON" period, a slight variation of hydraulic pressure on primary and secondary refiners was observed. One can therefore conclude that the CSF has been mainly controlled by the reject flow rate. Because in practice, the reject flow rate is periodically measured with short intervals (typically one minute), this parameter can be used to indirectly assess the reduction of variability of CSF.

Figure 15:
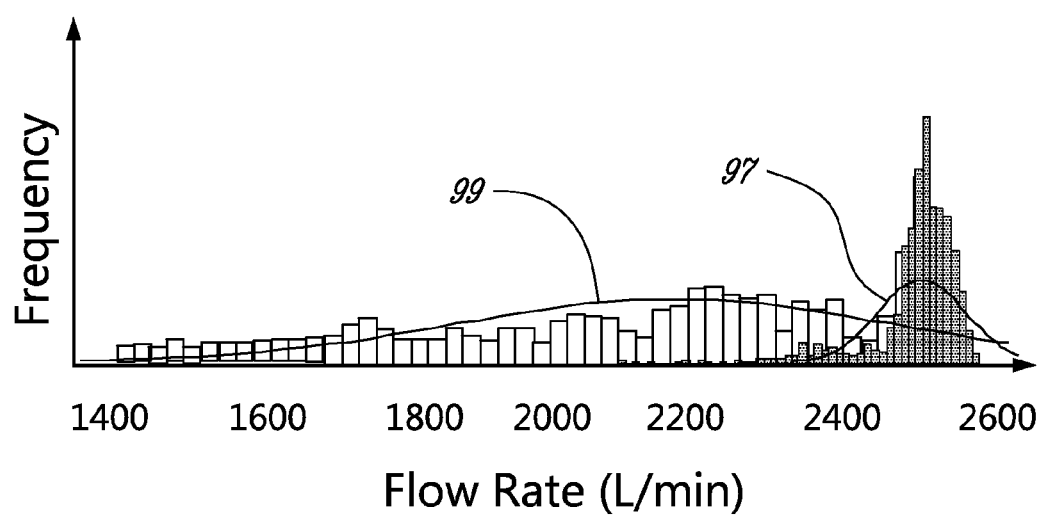
FIG. 15 is a graph comparing reject flow rate curves obtained without and with dry-based density stabilization.

Referring to FIG. 15, it can be seen that reject flow variability significantly decreased during the stabilization "ON" period as represented by curve 97. The reject flow rate in the stabilization "OFF" period as represented by curve 99 was 2199.42 (L/min) with a standard deviation of 204.80, while it was 2535.58 (L/min) with a standard deviation of 134.85 in the "ON" period. The increase of reject flow rate in the ON" period was due to the fact that the dry-based density was lower as compared with the "OFF" period.

In the pulp and paper industry, it has been recognized that there is an inverse relationship between freeness (CSF) and specific energy (SEC) applied to refining. The major disturbances that will affect the pulp quality are refining operation and chip qualities. Thus, by moving the average CSF toward the upper constraint, due to the inverse relationship to SEC, the specific energy is reduced. The stabilization of the dry-based density of chips gives rise to motor load and CSF stabilizations. Table 4 presents comparison refining data obtained without and with dry-mass stabilization.

TABLE 4

|  | without stabilisation («OFF») | | with stabilisation («ON») | | DIFERENCE | |
| --- | --- | --- | --- | --- | --- | --- |
|  | Average | S.D. | Average | S.D. | Average | S.D. |
| Sampling No. | 1395 |  | 1324 |  | 71 |  |
| Basic (kg/m³) | 438.8 | 11.31 | 428.6 | 6.90 | 10.2 | 4.41 |
| Production Rate. (o.d.t./d) | 343.47 | / | 355.13 | / | −11.66 | / |
| Motor Load (MW) | 31.21 | 0.50, | 30.80 | 0.40, | 0.41 | 0.1 |
| SEC (kW · h/t) | 2157.00 | / | 2066.96 | / | 90.04 | / |
| CSF (ml) | 206.45 | / | 227.24 | / | 20.79 | / |
| Reject Flow Rate (L/min) | 2199.42 | 204.80 | 2535.58 | 134.85 | −336.16 | 69.95 |
| Reject SEC (kW · h/t) | 321.66 | / | 358.99 | / | −37.33 | / |
| Total Energy | 2478.66 | / | 2425.95 | / |  | / |
| Energy Saving |  |  |  |  | 52.71 |  |

Figure 16:
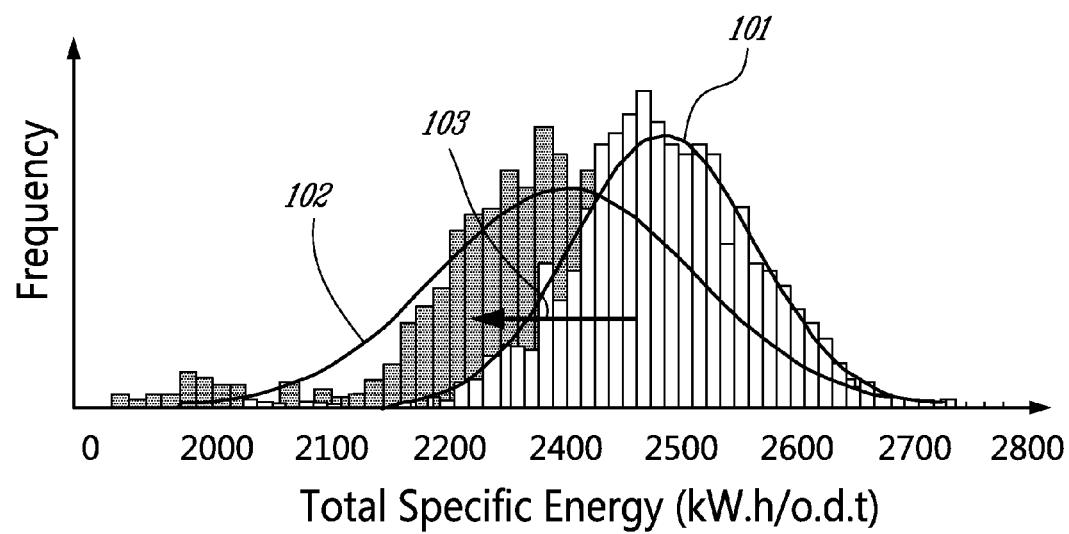
FIG. 16 is a graph comparing total specific energy consumption curves without and with dry-based density stabilization.

Since the dry-based density during the stabilization "ON" period was less than that observed during the "OFF" period (428.6 versus 436.8), the mill's process control system increased the CSF by 20.79 (ml), the production rate by 11.66 (o.d.t./d) and the reject rate by 336.16 (L/min), causing an increase of reject refining energy. The calculation of overall energy saving was taken into account in the graph of FIG. 16 comparing total specific energy consumption curves 101 and 102, respectively without and with dry-based density stabilization. An energy saving of 52.71 kW.h/o.d.t., representing a 2% gain as indicated by arrow 103, was obtained with dry-based density stabilization, corresponding to an economic saving for the mill of about $900 000 annually, based on electricity cost of 0.045 $/kW.h.

The invention claimed is:

1. A method for stabilizing dry-based density of wood chips to be fed to a chip processing stage upstream of a chip refining process from a plurality of independently discharging sources of wood chips characterized by one of a pure wood species and a mixture of wood species, said method comprising the steps of:
   i) estimating on-line a set of wood chip properties characterizing said wood chips to generate corresponding wood chip properties data, said set including at least one light reflection-related property, moisture content and dry-based density;
   ii) feeding said wood chip properties data at corresponding inputs of a reference model capable of comparing the estimated dry-based density with a predetermined dry-based density target to produce error data, and selectively modifying discharge rate set points of one or more of said wood chip sources to minimize the error data within fluctuation limits around the target; and
   iii) controlling the discharge rates of said wood chip sources in accordance with the set points to substantially stabilize the dry-based density of the wood chips.

2. The method of claim 1, wherein said at least one light reflection-related wood chip property data is expressed as at least one optical parameter representing light reflection characteristics of the wood chips.

3. The method of claim 2, wherein said optical parameter is luminance.

4. The method of claim 2, wherein said optical parameter is selected from the group consisting of hue, saturation, luminance and darkness indicator.

5. The method of claim 1, wherein said at least one light reflection-related wood chip property data is expressed as a plurality of optical parameters representing light reflection characteristics of the wood chips, including hue, saturation and luminance.

6. The method of claim 5, wherein said plurality of optical parameters further include darkness indicator.

7. The method of claim 1, wherein said dry-based density is estimated at said step i) from volume and weight measurements from said wood chips and from said moisture content.

8. A method for feeding wood chips at a substantially stable dry-based density to a processing stage upstream of a chip refining process from a plurality of independently discharging sources of wood chips being characterized by one of a pure wood species and a mixture of wood species, said method comprising the steps of:
   i) estimating on-line a set of wood chip properties characterizing said wood chips to generate corresponding wood chip properties data, said set including at least one light reflection-related property, moisture content and dry-based density;
   ii) feeding said wood chip properties data at corresponding inputs of a reference model capable of comparing the estimated dry-based density with a predetermined dry-based density target to produce error data, and selectively modifying discharge rate set points of one or more of said wood chip sources to minimize the error data within fluctuation limits around the target; and
   iii) controlling the discharge rates of said wood chip sources in accordance with the set points to feed said processing stage with the wood chips at said substantially stable dry-based density.

9. The method of claim 8, wherein said at least one light reflection-related wood chip property data is expressed as at least one optical parameter representing light reflection characteristics of the wood chips.

10. The method of claim 9, wherein said optical parameter is luminance.

11. The method of claim 9, wherein said optical parameter is selected from the group consisting of hue, saturation, luminance and darkness indicator.

12. The method of claim 8, wherein said at least one light reflection-related wood chip property data is expressed as a plurality of optical parameters representing light reflection characteristics of the wood chips, including hue, saturation and luminance.

13. The method of claim 12, wherein said plurality of optical parameters further include darkness indicator.

14. The method of claim 8, wherein said dry-based density is estimated at said step i) from volume and weight measurements from said wood chips and from said moisture content.

* * * * *